United States Patent
Ogundiwin et al.

(10) Patent No.: US 10,034,441 B2
(45) Date of Patent: Jul. 31, 2018

(54) MELON PLANTS WITH MELON YELLOWING ASSOCIATED VIRUS (MYAV) RESISTANCE

(71) Applicant: NUNHEMS B.V., AC Nunhem (NL)

(72) Inventors: Ebenezer Ogundiwin, Davis, CA (US); Dyeme Antônio Vieira Bento, Mossoró (BR); Peter Bernard Visser, Valencia (ES)

(73) Assignee: NUNHEMS B.V., Nunhem (NL)

( * ) Notice: Subject to any disclaimer, the term of this patent is extended or adjusted under 35 U.S.C. 154(b) by 82 days.

(21) Appl. No.: 14/651,485

(22) PCT Filed: Dec. 12, 2013

(86) PCT No.: PCT/EP2013/076454
§ 371 (c)(1),
(2) Date: Jun. 11, 2015

(87) PCT Pub. No.: WO2014/090968
PCT Pub. Date: Jun. 19, 2014

(65) Prior Publication Data
US 2015/0313107 A1      Nov. 5, 2015

(30) Foreign Application Priority Data

Dec. 12, 2012   (EP) .................................... 12196771
Apr. 4, 2013    (EP) .................................... 13162350

(51) Int. Cl.
| *A01H 5/08* | (2018.01) |
| *C12N 15/82* | (2006.01) |
| *C12Q 1/6895* | (2018.01) |
| *A01H 1/04* | (2006.01) |

(52) U.S. Cl.
CPC ................ *A01H 1/04* (2013.01); *A01H 5/08* (2013.01); *C12N 15/8283* (2013.01); *C12Q 1/6895* (2013.01); *C12Q 2600/156* (2013.01)

(58) Field of Classification Search
None
See application file for complete search history.

(56) References Cited

FOREIGN PATENT DOCUMENTS

| EP | 1800535 A1 | 6/2007 |
| EP | 1962578 B1 | 5/2011 |

OTHER PUBLICATIONS

Allen et al., "Transcript-specific, Single-nucleotide Polymorphism Discovery and Linkage Analysis in Hexaploid Bread Wheat (*Triticum aestivum* L.)", Plant Biotechnology Journal, 2011, vol. 9, pp. 1086-1099.

Ávila et al., "Produção do anti-soro e detecção por DAS-Elisa do Melon yellowing-associated virus em meloeiro", Tropical Plant Pathology, 2008, vol. 33, No. 3, pp. 245-247.

Boissot et al., "Mapping and Validation of QTLs for Resistance to Aphids and Whiteflies in Melon", Theor Appl Genet, 2010, vol. 121, No. 9, pp. 9-20.

Cuevas et al., A Consensus Linkage Map Identifies Genomic Regions Controlling Fruit Maturity and Beta-carotene-associated Flesh Color in Melon (*Cucumis melo* L.), Theor Appl Genet, 2009, vol. 119, pp. 741-756.

Diaz et al., A consensus Linkage Map for Molecular Markers and Quantitative Trait Loci Associated with Economically Important Traits in Melon (*Cucumis melo* L.), BMC Plant Biology 2011, vol. 11, No. 111, pp. 1-14.

Eduardo et al., "Estimating the Genetic Architecture of Fruit Quality Traits in Melon Using a Genomic Library of Near Isogenic Lines", J. Amer. Soc. Hort. Sci., 2007, vol. 132, NO. 1, pp. 80-89.

Eduardo et al., "Development of a genomic library of near isogenic lines (NILs) in melon (*Cucumis melo* L.) from the exotic accession PI161375," Theor. Appl Genet (2005) 112: pp. 139-148.

Fernandez-Silva et al., "Shaping Melons: Agronomic and Genetic Characterization of QTLs that Modify Melon Fruit Morphology", Theor Appl Genet (2010), vol. 121, pp. 931-940.

Garcia-Mas et al., The Genome of Melon (*Cucumis melo* L.), 2012,, PNAS, vol. 109, pp. 11872-11877.

Gonzalez et al., "Genome-wide BAC-end Sequencing of Cucumis melo Using Two BAC Libraries", BMC Genomics, 2010, vol. 11, No. 618, pp. 1-11.

International Search Report and Written Opinion issued in International Patent Application No. PCT/EP2013/076454 dated Dec. 13, 2014 (11 pages).

Ji et al., "Ty-3, A Begomovirus Resistance Locus Near the Tomato yello leaf curl virus Resistance Locus Ty-1 on Chromosome 6 of Tomato", Mol Breeding, 2007, vol. 20, pp. 271-284.

Lima et al., "Detecao por sorologia do Melon yellowing associated virus (MYaV) em áreas productoras de meláao no Nordeste brasileiro", Horticultura Brasileira, 2009, vol. 27, No. 4 (w/English abstract), pp. 478-483.

Nagata et al., "Analysis of the Tripple Gene Block Sequence in an Important Melon Pathogen, Melon Yellowing-associated Virus", J Gen Plant Pathol, 2010, vol. 76, pp. 268-272.

Nagata et al., "Isolation of a Novel Carlavirus from Melon in Brazil", Plant Pathology, 2003, vol. 52, p. 797.

Obando-Ulloa, et al., "Identification of QTLs Related to Sugar and Organic Acid Composition in Melon Using Near-isogenic Lines", Scientia Horticulturae, 2009, vol. 121, pp. 425-433.

Sebastian et al., "Cucumber (*Cucumis sativus*) and melon (*C. melo*) have numerous wild relatives in Asia and Australia, and the sister species of melon is from Australia", PNAS 2010, vol. 107, No. 32, pp. 14269-14273.

Verlaan et al., "Chromosomal Rearrangements Between Tomato and Solanum chilense Hamper Mapping and Breeding of The TYLCV Resistance Gene Ty-1", The Plant Journal, 2011, vol. 68, pp. 1093-1103.

*Primary Examiner* — Brent T Page
(74) *Attorney, Agent, or Firm* — Arent Fox LLP

(57) ABSTRACT

The present invention relates to the field of melon plants having Melon Yellowing associated Virus (MYaV) resistance.

25 Claims, 2 Drawing Sheets

MELON PLANTS WITH MELON YELLOWING ASSOCIATED VIRUS (MYAV) RESISTANCE

FIELD OF THE INVENTION

The present invention relates to the field of plant breeding, in particular melon breeding. The invention provides for the genetic locus conferring Melon Yellowing associated Virus (MYaV) resistance as found in wild melon accessions or in wild relatives of melon, and cultivated melon plants comprising said genetic locus (or a resistance conferring part thereof), which confers on said plants MYaV resistance. Also provided are seeds from which such plants can be grown, plant parts, cells, tissues or organs of such plants and breeding methods for transferring the MYaV resistance locus, or a resistance conferring part thereof, to other cultivated melon plants or plant cells, especially to MYaV susceptible melon plants. Also provided are molecular markers with which said genetic locus can be identified in plants and plant cells and/or transferred into other melon plants or plant cells. As the MYaV resistance present at the genetic locus is dominant, the MYaV resistant plants and/or plant cells may comprise the genetic locus in homozygous form or heterozygous form.

BACKGROUND OF THE INVENTION

Since 1999, a new disease which causes symptoms described as "yellowing of melon plants" was reported to cause damage in north-eastern Brazil, which is the region where more than 90% of the Brazilian melon production takes place. Symptoms are leaf mottling and yellowing and are mainly seen on older leaves (Nagata et al. 2003, Plant Pathology 52, 797). The virus causing this disease was tentatively named Melon yellowing-associated Virus (MYaV) (Nagata et al., 2003, supra and Nagata et al., 2005, Arch. Virology Vol. 150(2):379-87). In 2007 serological detection (using a polyclonal anti-bodies developed for MYaV detection, (see Avila et al. 2008 Trop. Plant Pathol. v. 33 n. 3 Brasilia May/June 2008) revealed that a large percentage of symptomatic melon plants were indeed infected with MYaV (Lima et al. Hortic. Bras. vol. 27 no. 4 Brasilia October/December 2009). The worst affected region was in the state Rio Grande do Norte, in Mossoro, with 96.3% of melons being infected. Interestingly, virus concentrations were higher in extracts prepared from stems of symptomatic plants than from leaves.

Figure 1:
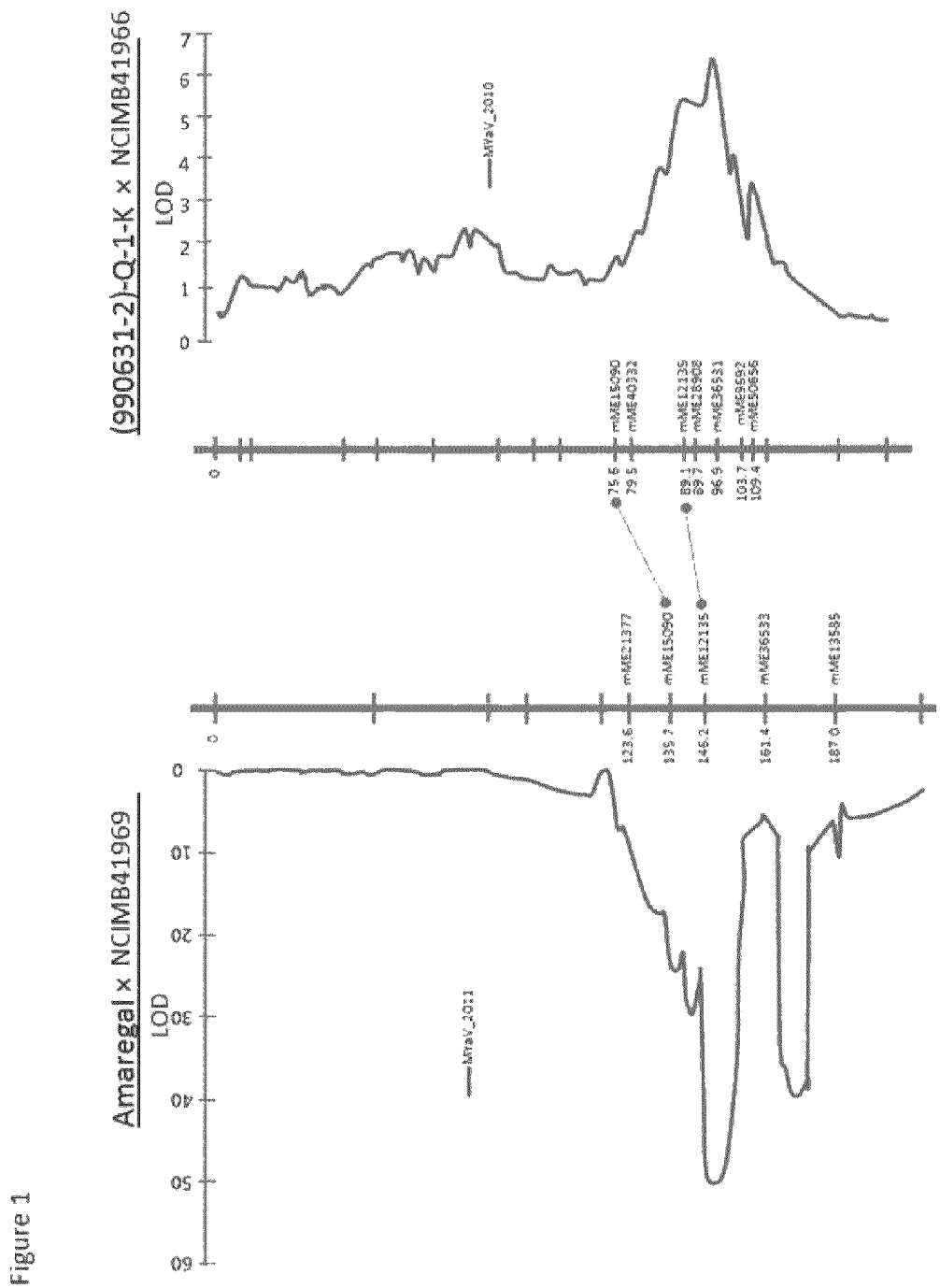

The typical symptoms of the disease appear as leaf mottling and yellowing, mainly of older leaves, similar to a nutritional disorder (see Nagata et al, 2003, supra and FIG. 1 of Nagata et al. 2010, Journal of General Plant Pathology Volume 76, No. 4, page 268-272). In infected leaf tissue showing yellowing symptoms filamentous virus particles of 600-700 nm length can be seen by electron microscopy.

The virus found in plants with the yellowing disease symptoms is transmitted from melon to melon plants by whiteflies (*Bemisia tabaci* biotype B). Also grafting can be used to transmit the virus to other melon plants or to *Cucumis anguria* (West Indian gherkin). By electron microscopy, long, filamentous *Carlavirus*-type particles and inclusion bodies were seen in infected leaves, which suggested the presence of a virus of the genus *Carlavirus* (Nagata et al. 2003, Plant Pathol 52:797). Nagata et al. 2005 (supra) sequenced two genes, the coat protein (ORF-A) and one more open reading frame (ORF-B), see GenBank Accession number AY373028. As Cowpea mild mottle virus (CPMMV) was the only *carlavirus* species known to be transmitted by whiteflies, genetic and serological properties of MYaV were expected to be similar to CPMMV. However, MYaV did not cross-react in a dot-immunobinding assay to antibody of CPMMV (Nagata et al. 2003, supra), and genomic sequence data showed that the coat protein (CP) of CPMMV was not closely related to that of MYaV (Nagata et al. 2005, supra).

Initially it was unclear whether to include MYaV within the *Carlavirus* genus or if it should be a new genus in the family Flexiviridae (Nagata et al. 2005, supra). However, in a recent study (Nagata et al. 2010, supra), an estimated 40% (ca. 3.1 kb) of the MYaV genome was cloned and sequenced and based on these data the authors suggest that the virus is indeed a new species within the genus *Carlavirus* and they suggest to change the name of this virus to Mellon Yellowing Virus (MYV). The 3.1 kb sequence contained 5 open reading frames (ORFs), encoding three Triple Gene Block proteins (TGB1, TGB2 and TGB3), the coat protein (CP) and putative nucleic acid binding protein (NABP), see GenBank Accession number AB510477. The coat protein (CP) sequence in this study had 93% sequence identity to the sequence of ORF-A (AY373028).

As no plants with resistance against the virus are available, one strategy developed to limit MYaV infection is to cover the whole field with spunbond nonwoven fabric layer from germination until flowering, to prevent whitefly transmission of the virus. However, plants became sensitive to leaf miners (*Liriomisa* spp.), which became widespread and heavily damaged fruit production (Nagata et al. 2010, supra).

It is an object of the invention to provide MYaV resistance sources and a genetic region comprising the resistance locus or a part thereof, which confer resistance against MYaV. It is a further object of the invention to provide cultivated melon plants (*Cucumis melo* L.) and cells, tissues, fruits and other parts of such plants comprising in their genome a MYaV resistance-conferring locus (or a resistance-conferring part thereof), either in homozygous or heterozygous form, whereby the melon plants are resistant against MYaV. Also seeds from which MYaV resistant melon plants can be grown are an embodiment of the invention.

In a further aspect molecular markers are provided, which can be used to detect the presence of and/or to transfer the MYaV resistance-conferring locus, or a resistance-conferring part thereof, in/into plants or plant cells of *Cucumis melo* L. One or more of the markers can, thus, for example be used to transfer the resistance locus, or a resistance-conferring part thereof, into melon plants which are susceptible to MYaV. In one embodiment the resistance locus, or resistance-conferring part thereof, is the locus on chromosome 6 as found in seeds deposited under accession number NCIMB 41966 or NCIMB 41969. In a further embodiment the resistance locus or resistance-conferring part thereof is the locus on chromosome 6, or a resistance-conferring part thereof, as found in other wild melon plants or wild relatives of melon.

One or more of the markers linked to, or associated with, the MYaV resistance locus, or resistance conferring part thereof, can also be used to identify new MYaV-resistance sources, such as other wild accessions of *Cucumis melo* or wild relatives of melon comprising an MYaV-resistance locus on chromosome 6 and for transferring (introgressing) the resistance locus, or a MYaV-resistance conferring part thereof, from such accessions into cultivated melon plants. The MYaV resistance conferring quantitative trait locus (QTL) on chromosome 6 (equivalent to ICuGI Linkage Group VI, or LG VI) was named MYaV6.1.

EP1962578B1 describes a CYSDV resistance QTL of PI313970 on a linkage group which is therein arbitrarily designated as LG6 and claims melon plants comprising an introgression from PI313970, which introgression comprises a CYSDV resistance QTL linked to at least one marker located on the chromosome equivalent to linkage group (LG) 6 of melon accession PI313970. It is noted that the in EP1962578B1 arbitrarily named LG6 is ICuGI LG VI of melon, but corresponds to ICuGI Linkage Group V (LG V). In one aspect the plant of the invention i.e. a cultivated *Cucumis melo* plant comprising resistance against Melon Yellowing associated Virus (MYaV) wherein said resistance is conferred by an introgression fragment on chromosome 6 in homozygous or heterozygous form and wherein said introgression fragment is from a wild plant of the species *Cucumis melo*, does not comprise the CYSDV resistance QTL as described in EP1962578B1. In another aspect the plant of the invention i.e. a cultivated *Cucumis melo* plant comprising resistance against Melon Yellowing associated Virus (MYaV) wherein said resistance is conferred by an introgression fragment on chromosome 6 in homozygous or heterozygous form and wherein said introgression fragment is from a wild plant of the species *Cucumis melo* does not comprise the markers E11/M49-239, as defined in paragraph [0037] of EP 1962578 B1. In yet another aspect the plant of the invention does not comprise the markers E11/M54-156, E14/M54-152, E14/M51-210, E14/M51-083, E11/M49-239, E11/M54-169, E14/M50-262, E11/M57-278, E11/M54-163 and/or E11/M49-072 as defined in paragraph [0040] of EP1962578 B1. In still another embodiment the plant of the invention does not comprise the markers E11/M54-156, E14/M54-152, E14/M51-210, E14/M51-083, E11/M49-239, E11/M64-169, E14/M60-262, E11/M67-278, E11/M64-163 and/or E11/M49-072 as defined in paragraph [0013] of EP 1962578 B1. The cited passages of EP1962578B1 are enclosed herein by reference. In still another aspect the plants of the invention, i.e. a cultivated *Cucumis melo* plant comprising resistance against Melon Yellowing associated Virus (MYaV) wherein said resistance is conferred by an introgression fragment on chromosome 6 in homozygous or heterozygous form and wherein said introgression fragment is from a wild plant of the species *Cucumis melo*, does not have a CYSDV phenotype (i.e. is not resistant to CYSCV).

GENERAL DEFINITIONS

The indefinite article "a" or "an" does not exclude the possibility that more than one of the element is present, unless the context clearly requires that there be one and only one of the elements. The indefinite article "a" or "an" thus usually means "at least one".

As used herein, the term "plant" includes the whole plant or any parts or derivatives thereof, such as plant organs (e.g., harvested or non-harvested storage organs, tubers, fruits, leaves, seeds, etc.), plant cells, plant protoplasts, plant cell or tissue cultures from which whole plants can be regenerated, plant calli, plant cell clumps, and plant cells that are intact in plants, or parts of plants, such as embryos, pollen, ovules, ovaries, fruits (e.g., harvested tissues or organs, such as harvested melon fruits or parts thereof), flowers, leaves, seeds, tubers, bulbs, clonally propagated plants, roots, rootstocks, stems, root tips and the like. Also any developmental stage is included, such as seedlings, immature and mature, etc. When "seeds of a plant" are referred to, these either refer to seeds from which the plant can be grown or to seeds produced on the plant, after self-fertilization or cross-fertilization.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous). Thus, for example reference may herein be made to a MYaV-allele of the MYaV resistance locus MYaV6.1.

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

The term "locus" (loci plural) means a specific place or places or a site on a chromosome where for example a gene or genetic marker is found. The MYaV resistance locus (or MYaV resistance-conferring locus) is, thus, the location in the genome of melon, where the MYaV-resistance gene is found. In cultivated melon the MYaV resistance locus is found on chromosome 6 (using the ICuGI nomenclature for chromosome or Linkage Groups, i.e. LGVI) and is preferably introgressed into the cultivated melon genome (i.e. onto chromosome 6, or LGVI) from wild melon accessions, such as (but not limited to) the two wild melon accessions deposited under accession numbers NCIMB 41966 and NCIMB41969, or from other wild melons or wild relatives of melon which are crossable with *C. melo* and from which crosses fertile offspring can be produced.

A "quantitative trait locus", or "QTL" is a chromosomal locus that encodes for one or more alleles that affect the expressivity of a continuously distributed (quantitative) phenotype. The MYaV resistance conferring quantitative trait locus is named herein MYaV6.1.

"ICuGI" refers to the International Cucurbit Genomics Initiative, which publishes genetic maps of e.g. *Cucumis melo* (http://www.icugi.org/cgi-bin/cmap/map_set_info?species_acc=CM). The current version of the *C. melo* genome map is of Mar. 4, 2012 and the map of chromosome 6 is referred to as ICuGI_VI (or LG VI, or Linkage Group VI) and contains 124 markers (11 AFLP, 1 ISSR, 19 RAPD, 17 RFLP, 31 SNP, 45 SSR markers) on a linkage group spanning 0.00 to 98.00 cM. Herein melon chromosome 6 and LG VI are used interchangeably.

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Physical distance" between loci (e.g. between molecular markers and/or between phenotypic markers) on the same chromosome is the actually physical distance expressed in base pairs (bp), kilo base pairs (kb) or megabase pairs (Mb). *C. melo* has a total haploid genome size of about 450 Mb, divided into 12 chromosome pairs, see Garcia-Mas et al, PNAS Jul. 2, 2012, p 1-6 and Gonzales et al. 2010, BMC Genomics 11:339, p 1-13.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). In melon, wild melon accessions or wild relatives of melon are often used to introgress fragments of the wild genome into the genome of cultivated melon, *Cucumis melo*. Such a cultivated melon plant thus has a "genome of cultivated *C. melo*", but comprises in the genome a fragment of a wild melon or of a wild relative of melon, e.g. an introgression fragment of a related wild *Cucumis* genome, such as *Cucumis melo* ssp. *agrestis*, *C. melo* ssp. *melo*, *C. melo* ssp. *acidulous*, *C. callosus*, *C. trigonus*, *C. picrocarpus*, or another wild melon or wild relative of melon. It is understood that the term "introgression fragment" never includes a whole chromosome, but only a part of a chromosome. The introgression fragment can be large, e.g. even half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

The "MYaV-allele" refers to a MYaV resistance-conferring allele found at the MYaV resistance-conferring locus MYaV6.1, or at the resistance-conferring part of the locus, introgressed into cultivated melon (onto cultivated *C. melo* chromosome 6) from a wild melon or wild relative of melon, e.g. from plants of which a representative sample of seeds were deposited under accession number NCIMB 41966 or NCIMB 41969. The term "MYaV-allele", thus, also encompasses MYaV-alleles obtainable from other MYaV resistant *Cucumis* accessions, such as MYaV orthologous alleles (see below). When one or two MYaV-alleles are present at the MYaV resistance-conferring locus in the genome (i.e. in heterozygous or homozygous form), the plant is resistant against MYaV, i.e. has a MYaV resistance phenotype. In cultivated melon plant lacking the introgression fragment, the *C. melo* allele found at the same locus on chromosome 6 is herein referred to as "myav" allele (or MYaV-susceptible allele). As the resistance is dominant, myav/myav plants show a MYaV-susceptible phenotype, whereas MYaV/myav plants and MYaV/MYaV plants are plants which possess the MYaV resistant phenotype conferred by the MYaV-allele (i.e. are resistant to MYaV).

"MYaV orthologous alleles" or "MYaV orthologs" or "orthologs of MYaV" are alleles of MYaV resistance genes present in other wild relatives of melon, on the orthologous chromosomes 6. Such ortholgous alleles may, thus, be found on orthologous chromosome 6 of wild relatives of *C. melo*, such as *C. callosus, C. trigonus, C. picrocarpus* and others and are transferable, by introgression, onto *C. melo* chromosome 6.

A "MYaV resistance phenotype" or "MYaV resistance" or "MYaV resistant plants" refers to resistance against MYaV conferred by the MYaV allele (or by the MaYaV orthologous allele) when present in the *C. melo* genome in two copies (in homozygous from). The MYaV resistance phenotype and the presence of the MYaV/allele and/or orthologs of MYaV can be tested using the "MYaV resistance assay" and/or the MYaV marker assays.

Figure 2:
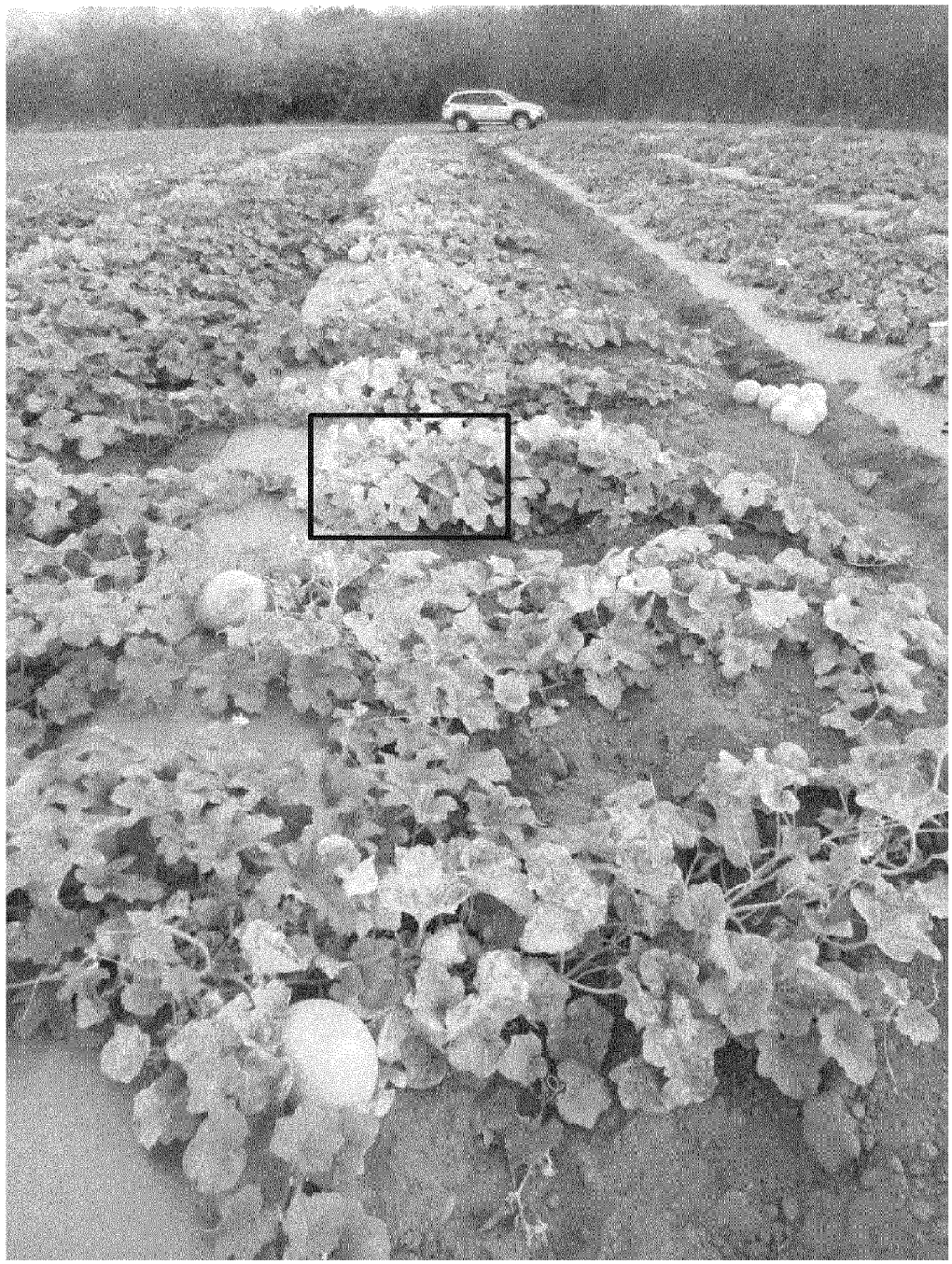

A "MYaV resistance assay" can be carried out in different ways, either by grafting or, preferably, as a field test, as also described elsewhere herein. Preferably a field assay is used in an area of natural high incidence of *Bemisia tabaci* biotype B carrying MYaV, such as north-eastern Brazil, or other areas where a high disease incidence of MYaV is present (i.e. an MYaV infested area). A plant of a particular genotype is considered to be MYaV-resistant if the average disease-resistance score of a plurality of plants (at least 4, 5, 6, 7, 8, 9, 10 or more, in preferably at least two or three replicates) of that genotype is significantly higher compared to the susceptible controls (plants lacking an introgression fragment which comprises an MYaV-allele or an MYaV-ortholog, such as Galia melon varieties Amaregal F1 (Nunhems) or Glory (Origene Seeds); or Piet de Sapo melon varieties Medellin (Nunhems) or Sancho (Syngenta)), when grown in the same environment. Thus, for example, melon plants of a line comprising the introgression of the MYaV-resistance conferring locus, or a resistance conferring part thereof, in heterozygous or homozygous form may be grown together with suitable control melon plants (especially MYaV-susceptible melon plants) in an open field in north-eastern Brazil and when all plants of susceptible controls show clear yellowing symptoms (see FIG. 2) all plants are phenotyped on a disease-resistance scale of 1 (totally yellow leaves, i.e. leaves in the first $\frac{1}{3}^{rd}$ of the plant are 100% yellow) to 9 (totally green leaves; leaves in the first $\frac{1}{3}^{rd}$ of the plant are 100% green), whereby 2=about 81% to 99% of leaf area in the first $\frac{1}{3}^{rd}$ of the plant is yellow, 3=about 65% to 80% of leaf area in the first $\frac{1}{3}^{rd}$ of the plant is yellow, 4=about 49% to 64% of leaf area in the first $\frac{1}{3}^{rd}$ of the plant is yellow, 5=about 33% to 48% of leaf area in the first $\frac{1}{3}^{rd}$ of the plant is yellow, 6=about 17% to 32% of leaf area in the first $\frac{1}{3}^{rd}$ of the plant is yellow, 7=up to about 17% of leaf area in the first $\frac{1}{3}^{rd}$ of the plant is yellow, 8=few leaves in the first $\frac{1}{3}^{rd}$ of the plant start to show yellow shadow/ mottling. The first ⅓$^{rd}$ of the plant refers to the older leaves in the first ⅓$^{rd}$ area of the plant as determined from the main stem/root system of the plant and as seen in FIG. 2 (black rectangle). The younger leaves on the vines, further towards the tip of the vines, are not phenotyped, as these are generally green at the moment of phenotyping and turn yellow only on susceptible plants after several more days, e.g. 7-10 days later (although they do already contain the virus at the moment of phenotyping). Plants with an average disease-resistance score that is significantly higher than the average disease score of the susceptible controls, e.g. an average score of at least 3.0, preferably at least 4.0, more preferably at least 5.0, at least 6.0, at least 7.0, at least 8.0, most preferably 9.0, are herein MYaV-resistant plants or plants having an MYaV resistance.

The "MYaV-marker assay" is a molecular marker assay which can be used to test whether on C. melo chromosome 6 an introgression from a wild melon, or wild relative of melon, comprising the MYaV-allele is present in the genome (or whether in wild melon or wild relatives of melon comprise the MYaV6.1 QTL-comprising region in their genome), by determining the genotype of SNP markers mME15090 and/or mME12135, and/or any wild melon or wild-relative of melon genome-specific marker in between SNP markers mME15090 and mME12135, and optionally also either A) of one or more markers selected from the group mME40332, mME28908, mME36531, mME9692, mME50656, or any wild-C. melo-genome or wild melon relative genome-specific marker between mME1509 and mME50656, or B) of one or more markers selected from the group mME21377, mME36533, mE13585, or any wild C. melo-genome specific marker or wild melon relative genome-specific between mME21377 and mME13585.

"Melon" or "muskmelon" refers herein to plants of the species Cucumis melo. Melons or 'muskmelons', Cucumis melo, can be classified into: C. melo cantalupensis, C. melo inodorous and C. melo reticulatus. C. melo cantalupensis are also referred to as Cantaloupes and are primarily round in shape with prominent ribs and almost no netting. Most have orange, sweet flesh and they are usually very fragrant. In contrast to the European cantaloupe, the North American 'Cantaloupe' is not of this type, but belongs to the true muskmelons. C. melo inodorous (or winter melons) can be subdivided into different types, such as Honeydew melon, Piel de Sapo, Sugar melon, Japanese melon, etc. C. melo reticulatus is the true muskmelon, with reticulated skin (netted) and includes Galia melons, Sharlyn melons and the North American cantaloupe.

"Cultivated melon" refers to plants of Cucumis melo i.e. varieties, breeding lines or cultivars of the species C. melo, cultivated by humans and having good agronomic characteristics, especially producing edible and marketable fruits of good size and quality and uniformity; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

Melon and the wild relatives of melon is/are diploid and has/have 12 pairs of homologous chromosomes, numbered 1 to 12. "Melon chromosome 6" refers to the C. melo chromosome 6, as known in the art and as referred to by the ICuGI nomenclature. "Orthologous chromosome 6" refers to the chromosome 6 of wild relatives of melon, parts of which can be introgressed into cultivated melon chromosome 6.

"Wild melon" includes wild plants of the species Cucumis melo, e.g. C. melo ssp agrestis, C. melo ssp. melo, C. melo var. texanus, C. melo var. acidulous, seeds deposited under NCIMB 41966, NCIMB 41969, and other wild C. melo accessions, as e.g. landraces or PI accessions found on http://www.ars-grin.gov or other seed collections. Seeds deposited under NCIMB 41966 were obtained from the ARS-GRIN collection and have as designated origin 'India'. Seeds deposited under NCIMB 41969 were obtained from Spain and have as origin Uzbekistan.

"Wild relatives of melon" include wild plants of other Cucumis species, but which can be crossed with Cucumis melo to produce fertile offspring (optionally with the aid of embryo rescue, temperature-dependent enhancement of pollen-tube growth, or similar techniques to overcome reproductive barriers) and from which chromosome fragments can be obtained and transferred into Cucumis melo (either by interspecific crosses with C. melo or via crosses with a bridge species). Examples of wild relatives of melon are C. anguria, C. metuliferus, Cucumis callosus, Cucumis trigonus, Cucumis ficifolius, C. picocarpus, C. zeyheri, C. africanus, C. meeusei, C. prophetarum, C. hystrix, C. queenslandicus, and other Cucumis species (see e.g. Sebastian et al. 2010, PNAS Vol 107, no. 32, 14269-14273).

"Average" refers herein to the arithmetic mean.

A "recombinant chromosome" refers to a chromosome having a new genetic makeup arising through crossing over between homologous chromosomes, e.g. a "recombinant chromosome 6", i.e. a chromosome 6 which is not present in either of the parent plants and arose through a rare crossing-over event between homologous chromosomes of a chromosome 6 pair. Herein, for example, a recombinant melon chromosome 6 comprising a MYaV-resistance conferring locus, or resistance-conferring part thereof (comprising a MYaV-resistance allele), is provided.

The term "traditional breeding techniques" encompasses herein crossing, backcrossing, selfing, selection, double haploid production, embryo rescue, protoplast fusion, marker assisted selection, mutation breeding etc. as known to the breeder (i.e. methods other than genetic modification/transformation/transgenic methods), by which, for example, a recombinant chromosome 6 can be obtained, identified and/or transferred.

"Backcrossing" refers to a breeding method by which a (single) trait, such as MYaV resistance, can be transferred from an inferior genetic background (e.g. a wild melon or wild relative of melon; also referred to as "donor") into a superior genetic background (also referred to as "recurrent parent"), e.g. cultivated melon. An offspring of a cross (e.g. an F1 plant obtained by crossing a wild, MYaV-resistant melon with a cultivated, MYaV-susceptible melon; or an F2 plant or F3 plant, etc., obtained from selfing the F1) is "backcrossed" to the parent with the superior genetic background, e.g. to the cultivated, MYaV-susceptible, parent. After repeated backcrossing, the trait of the inferior genetic background will have been incorporated into the superior genetic background.

"Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically linked to an MYaV-resistance locus, can be used to detect and/or select melon plants comprising the MYaV-resistance locus. The closer the genetic linkage of the molecular marker to the locus (e.g. about 7 cM, 6 cM, 5 cM, 4 cM, 3 cM, 2 cM, 1 cM, 0.5 cM or less), the less likely it is that the marker is dissociated from the locus through meiotic recombination.

"LOD-score" (logarithm (base 10) of odds) refers to a statistical test often used for linkage analysis in animal and plant populations. The LOD score compares the likelihood of obtaining the test data if the two loci (molecular markers loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation.

"Cell culture" or "tissue culture" refers to the in vitro culture of cells or tissues of a plant.

"Regeneration" refers to the development of a plant from cell culture or tissue culture or vegetative propagation.

"Transgene" or "chimeric gene" refers to a genetic locus comprising a DNA sequence, such as a recombinant gene or a recombinant chromosome or part thereof, which has been introduced into the genome of a melon plant by transformation, such as *Agrobacterium* mediated transformation. A plant comprising a transgene stably integrated into its genome is referred to as "transgenic plant". A transgene or transgenic plant may also contain a complete recombinant chromosome or part of a recombinant chromosome, e.g. the part comprising the MYaV-allele, introduced into the genome by transformation.

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

DETAILED DESCRIPTION OF THE INVENTION

The present invention relates to a cultivated *Cucumis melo* plant comprising resistance against Melon Yellowing associated Virus (MYaV). In particular, the resistance is conferred by an introgression fragment on melon chromosome 6, wherein said introgression fragment is from a wild plant of the species *Cucumis melo* or from a wild relative of melon.

The present inventors crossed two different wild *C. melo* accessions, representative seeds of which were deposited under NCIMB 41966 and NCIMB 41969, to a MYaV-susceptible melon breeding line and to a susceptible melon variety, respectively, and carried out QTL-mapping, based on phenotyping data obtained from MYaV-infested fields near Mossoro (Rio Grande do Norte, Brazil).

Surprisingly, in both mapping populations, a highly significant QTL for MYaV resistance was found on melon chromosome 6, indicating that different wild *Cucumis melo* accessions comprise a MYaV resistance locus on chromosome 6, which was transferred into cultivated *C. melo* and conferred MYaV-resistance onto the cultivated melon plant. In the two mapping populations the QTL, which was named MYaV6.1, explained 32.6% and 91.7% of the observed phenotypic variation for MYaV resistance, and is therefore highly significant.

It is noted that when reference herein is made to a (one) QTL (MYaV6.1) or to a MYaV resistance conferring locus (or a resistance conferring part thereof) on chromosome 6 of the *C. melo* genome, it can be that there are in fact two (or more) QTLs linked to each other on chromosome 6, as the LOD-score has two peaks in both mapping populations (see FIG. 1). So reference to one QTL or to one locus encompasses the possibility that there are two (or more) QTLs or two (or more) loci coupled to each other on chromosome 6. Equally reference herein to an introgression fragment on chromosome 6 having a QTL or an MYaV-resistance conferring locus (or resistance-conferring part thereof) encompasses that the introgression fragment comprises all resistance-conferring loci, or in cases of smaller introgression fragments, at least a large enough introgression region (with one, two or more QTLs) so that MYaV-resistance is conferred by the introgression fragment when the introgression fragment is in heterozygous or homozygous form in the *C. melo* genome. Thus, in case of smaller introgression fragments, the introgression fragment comprises preferably at least the major QTL (i.e. the larger of the two LOD-peaks in FIG. 1).

Thus, in one aspect, it was found that a Quantitative Trait Loci (QTL MYaV6.1) which confers MYaV-resistance is present on chromosome 6 of wild melons and that this QTL, when transferred (introgressed) into a cultivated, MYaV-susceptible melon variety or breeding line, and when present in heterozygous or homozygous form, confers MYaV-resistance onto the cultivated melon plant. The QTL, or the introgression fragment comprising the QTL (comprising the MYaV-resistance allele), is thus dominant, i.e. it is sufficient to have the introgression fragment on one of the chromosomes 6 (one recombinant chromosome 6), while the homologous chromosome 6 of the pair may be a (non-recombinant) chromosome 6 of cultivated *C. melo* lacking the introgression fragment.

Although the present sources of MYaV-resistance allele introgressions are two wild sources (NCIMB 41966 and NCIMB 41969, from India and Uzbekistan, respectively), there are likely other wild *Cucumis* accessions which comprise MYaV-alleles or MYaV orthologous alleles at the same locus on chromosome 6. Such MYaV-alleles or MYaV-orthologous alleles can also be identified and introgressed into cultivated *C. melo* as described herein, to generate a cultivated *C. melo* plant comprising a genome of *C. melo* and a recombinant chromosome 6, whereby the recombinant chromosome 6 comprises a wild *Cucumis* species introgression fragment, which confers an MYaV-resistance phenotype onto the cultivated *C. melo* plant when present in homozygous or heterozygous form.

Accessions of wild melons and wild relatives of melon, such as accessions obtainable from the USDA National Plant Germplasm System collection or other seed collections, can be screened for MYaV resistance using phenotypic and/or MYaV-marker assays, and resistant accessions can be crossed with a *Cucumis melo* plant lacking MYaV resistance. The F2 generation (or further generation, such as the F3 or a backcross generation) can then be screened for recombinant plants having the MYaV resistance phenotype and/or the introgression fragment or a part thereof, using the molecular marker assays described herein.

Plants, Seeds and Plant Parts According to the Invention

Thus, in a first embodiment a cultivated *Cucumis melo* plant comprising resistance against Melon Yellowing associated Virus (MYaV) is provided.

The presence of an MYaV resistance phenotype can be determined using the MYaV resistance assay, whereby plants are screened for resistance under natural field conditions in one or more areas where MYaV incidence is high, such as north-eastern Brazil. Plants according to the invention have MYaV resistance if their average disease score, on a scale of 9=totally green leaves (in the first $\frac{1}{3}^{rd}$ of the plant) to 1=totally yellow leaves (in the first $\frac{1}{3}^{rd}$ of the plant), is significantly higher than the average disease score of MYaV susceptible varieties, when grown under the same environmental conditions. The average disease score of MYaV resistant cultivated melon plants is, in one embodiment, at least 3, preferably at least 4, on a scale of 1=totally yellow leaves to 9=totally green leaves, when grown in the field in north-eastern Brazil, or in any other field where MYaV incidence is high. In another embodiment, the average disease score is at least 5, 6, 7, 8 or 9. Whether the MYaV incidence is high can be either seen due to the severe yellowing symptoms (average disease score=1) developing on the susceptible control plants, such as cultivars Sancho, Amaregal, or others. Alternatively or in addition MYaV virus levels can be determined in melon tissue, e.g. using polyclonal anti-bodies developed for MYaV detection.

Average disease scores are preferably calculated based on at least four plants of a line or variety, preferably at least 5, 10, 15, 20 or more plants grown under the same environmental conditions.

The resistance against MYaV is conferred by an introgression fragment on chromosome 6, wherein the introgression fragment is derived from a wild melon genome or from a wild relative of melon. The introgression fragment comprises the Quantitative trait locus (QTL) referred herein to as MYaV6.1, which locus in turn comprises a MYaV-resistance allele, or a MYaV-orthologous resistance allele, of the MYaV resistance gene.

The cultivated melon plants according to the invention, thus, have a recombinant chromosome 6, which comprises an introgression fragment of a wild melon chromosome 6 or of an orthologous chromosome 6 of a wild relative of melon.

As the resistance is dominant, the resistance phenotype is seen when the resistance allele is in heterozygous or homozygous form, the cultivated melon plants according to the invention have the introgression fragment, or the resistance-conferring part thereof, on chromosome 6 in heterozygous or homozygous form.

The introgression fragment is derivable from (or derived from) or obtainable from (or obtained from) a wild plant of the species *Cucumis melo*, which comprises the MYaV QTL (MYaV6.1) on chromosome 6. Alternatively, the introgression fragment is derivable from (or derived from) or obtainable from (obtained from) a wild relative of *Cucumis melo*, which can be crossed with *Cucumis melo* (optionally using embryo rescue or other techniques to aid production of viable offspring), so that the fragment of the orthologous chromosome 6 can be introgressed into the chromosome 6 of *C. melo*, especially cultivated *C. melo*.

In a specific embodiment, the introgression fragment comprising the MYaV resistance locus is derivable from (or derived from) or obtainable from (or obtained from) wild *C. melo* plants, a representative sample of seeds of which has been deposited under accession number NCIMB 41966 or NCIMB41969. In one aspect the invention provides a cultivated *C. melo* plant which comprises resistance against MYaV, wherein the resistance is conferred by an introgression fragment on melon chromosome 6, wherein said introgression fragment (conferring said MYaV resistance) is obtained by (or obtainable by) crossing a plant of which seeds were deposited under Accesssion number NCIMB 41966 or NCIMB41969 with a cultivated melon plant. Both these wild *C. melo* accessions have a MYaV-resistance phenotype, with an average disease score of 9.0 (leaves remain green), compared to an average disease score of below 2.0, or below 1.5, for the susceptible melon varieties, such as Amaregal F1. The introgression fragment may also be derived from (or obtained from) other wild *C. melo* plants or other wild relatives of melon, which have an average MYaV disease score of at least 7, preferably at least 8, more preferably 9, as e.g. determined in the MYaV resistance assay.

In another embodiment the invention relates to a plant of the invention i.e. a cultivated *Cucumis melo* plant comprising resistance against Melon Yellowing associated Virus (MYaV) wherein said resistance is conferred by an introgression fragment on chromosome 6 in homozygous or heterozygous form and wherein said introgression fragment is from a wild plant of the species *Cucumis melo* wherein the introgression fragment is identical as the MYaV resistance conferring fragment on chromosome 6 as present in seeds deposited under number NCIMB 41966, NCIMB 41969, NCIMB 42113, or NCIMB 42198.

The skilled person is capable of identifying and introgressing the MYaV6.1 QTL comprising region found in other wild melon accessions or other wild relatives of melon into cultivated *C. melo* as will be explained further below. The skilled person is also able to identify other molecular markers linked to (associated with) the QTL, which can be used to identify the presence of an introgression fragment from such other wild melons or wild relatives of melon on chromosome 6 of *C. melo*. Two of the molecular markers provided herein were found to be associated with the MYaV-resistance QTL, where the introgression fragment was obtained from two different wild sources. These two markers may also be linked to (associated with) MYaV resistance on chromosome 6, or on orthologous chromosomes 6, and may thus be useful to derive the QTL from different sources. Alternatively, the skilled person can identify other molecular markers using known methods.

In one embodiment the presence of the introgression fragment, or the chromosome 6 region (or orthologous chromosome 6 region), comprising the MYaV resistance locus, is detectable by a molecular marker assay which detects at least one, preferably at least the following two Single Nucleotide Polymorphism (SNP) markers:

a) the CC or AC genotype for the SNP marker mME15090 in SEQ ID NO: 1 (or SEQ ID NO: 9);

b) the AA or AG genotype for the SNP marker mME12135 in SEQ ID NO: 3 (or SEQ ID NO: 10).

As mentioned, these two SNP markers were found to be genetically linked to (or associated with) the introgression fragment on chromosome 6 comprising the QTL MYaV6.1 in both mapping populations, i.e. in plants comprising the resistance QTL from two different wild melon accessions.

Thus, in one embodiment the MYaV resistant plants according to the invention comprise at least a Cytosine (C) (i.e. the CC or AC genotype) instead of two Adenines (AA) at nucleotide 71 of SEQ ID NO:1 (or SEQ ID NO:9) (referred to as SNP marker mME15090) and/or they comprise at least a Adenine (A) (i.e. the AA or AG genotype) instead of two Guanines (GG) at nucleotide 71 of SEQ ID NO: 3 (or SEQ ID NO: 10) (referred to as SNP marker mME12135). The SNP genotype refers to two nucleotides, and genomic sequences comprising one of these two nucleotides, one on each chromosome 6. So a plant having a CC genotype for mME15090 has an identical nucleotide (C) on both chromosomes, while a plant having an AC genotype for mME15090 has one chromosome with an A at nucleotide 71 of SEQ ID NO: 1 and one chromosome with a C at nucleotide 71 of SEQ ID NO: 1.

In a further embodiment, the introgression fragment, or the chromosome 6 region (or orthologous chromosome 6 region) comprising the MYaV-resistance locus, is detectable by a molecular marker assay which further detects at least one, two, three, four, five, six, seven or all eight of the Single Nucleotide Polymorphism (SNP) markers selected from the group consisting of:
a) the GG or AG genotype for the SNP marker mME40332 in SEQ ID NO: 2;
b) the TT or AT genotype for the SNP marker mME28908 in SEQ ID NO: 4;
c) the TT genotype for the SNP marker mME36531 in SEQ ID NO: 5;
d) the AA or AT genotype for the SNP marker mME9692 in SEQ ID NO: 6;
e) the CC or CT genotype for the SNP marker mME50656 in SEQ ID NO: 7;
f) the AA or AG genotype for the SNP marker mME21377 in SEQ ID NO: 8;
g) the TT or GT genotype for the SNP marker mME36533 in SEQ ID NO: 11;
h) the TT or CT genotype for the SNP marker mME13585 in SEQ ID NO: 12.

Thus, the MYaV-resistant melon plant according to the invention further comprises at least a Guanine (G) (i.e. the GG or AG genotype) instead of two Adenines (AA) at nucleotide 71 of SEQ ID NO: 2 (referred to as SNP marker mME40332), and/or at least a Thymine (T) (i.e. the TT or AT genotype) instead of two Adenines (AA) at nucleotide 71 of SEQ ID NO: 4 (referred to as SNP marker mME28908), and/or two Thymines (TT) (i.e. the TT genotype) instead of two Cytosines (CC) or instead of CT at nucleotide 71 of SEQ ID NO: 5 (referred to as SNP marker mME36531), and/or at least an Adenine (A) i.e. the AA or AT genotype) instead of two Thymines (TT) at nucleotide 71 of SEQ ID NO: 6 (referred to as SNP marker mME9692), and/or at least a Cytosine (C) (i.e. the CC or CT genotype) instead of two Thymines (TT) at nucleotide 71 of SEQ ID NO: 7 (referred to as SNP marker mME50656), and/or at least a Adenine (A) i.e. the AA or AG genotype) instead of two Guanines (GG) at nucleotide 71 of SEQ ID NO: 8 (referred to as SNP marker mME21377), and/or at least a Thymine (T) (i.e. the TT or GT genotype) instead of two Guanines (GG) at nucleotide 71 of SEQ ID NO: 11 (referred to as SNP marker mME36533), and/or at least a Thymine (T) (i.e. the TT or CT genotype) instead of two Cytosines (CC) at nucleotide 71 of SEQ ID NO: 12 (referred to as SNP marker mME13585).

In one aspect, the introgression fragment, or the chromosome 6 region (or orthologous chromosome 6 region) comprising the MYaV-resistance locus, which is detectable by the above markers is from a wild plant of the species *Cucumis melo*, and in one aspect it is from a plant of which a representative sample of seeds has been deposited under accession number NCIMB 41966 and NCIMB 41969, thus the QTL, and the chromosome 6 region comprising the QTL, is in one aspect the QTL as found in NCIMB 41966 or in NCIMB 41969. In one aspect the introgression fragment, or the recombinant chromosome 6, is obtained from crossing a plant grown from seeds deposited under accession number NCIMB 41966 or NCIMB 41969 with another melon plant, especially a cultivated melon plant of the species *C. melo*.

Thus, in one aspect the MYaV-resistant melon plant according to the invention comprises an introgression fragment on chromosome 6, which is obtainable from seeds of which a representative sample has been deposited under NCIMB 41966 and wherein said introgression fragment comprises at least two, optionally at least 3, 4, 5, 6 or 7, SNP markers selected from the group consisting of:
a) the CC or AC genotype for the SNP marker mME15090 in SEQ ID NO: 1;
b) the GG or AG genotype for the SNP marker mME40332 in SEQ ID NO: 2;
c) the AA or AG genotype for the SNP marker mME12135 in SEQ ID NO: 3.
d) the TT or AT genotype for the SNP marker mME28908 in SEQ ID NO: 4;
e) the TT genotype for the SNP marker mME36531 in SEQ ID NO: 5;
f) the AA or AT genotype for the SNP marker mME9692 in SEQ ID NO: 6;
g) the CC or CT genotype for the SNP marker mME50656 in SEQ ID NO: 7.

In another aspect the MYaV-resistant melon plant according to the invention comprises an introgression fragment on chromosome 6, which is obtainable from seeds of which a representative sample has been deposited under NCIMB 41969 and wherein said introgression fragment comprises at least two, optionally at least 3, 4 or 5 SNP markers selected from the group consisting of:
a) the AA or AG genotype for the SNP marker mME21377 in SEQ ID NO: 8;
b) the CC or AC genotype for the SNP marker mME15090 in SEQ ID NO: 9;
c) the AA or AG genotype for the SNP marker mME12135 in SEQ ID NO: 10;
d) the TT or GT genotype for the SNP marker mME36533 in SEQ ID NO: 11;
e) the TT or CT genotype for the SNP marker mME13585 in SEQ ID NO: 12.

To obtain the introgression fragment from the deposited seeds, a plant is grown from the seed and the plant is crossed with a susceptible *C. melo* plant to obtain F1 seeds. The F1 hybrid seed and plants grown therefrom, contain one chromosome 6 from the susceptible parent (without QTL MYaV6.1) and one chromosome 6 from the wild MYaV-resistant parent. To generate recombination events between these two homologous chromosomes 6, meiosis needs to take place and plants comprising the recombinant chromosomes 6 need to be identified. For example, the F1 can be selfed to produce F2 plants, and/or resistant F2 plants or F3 plants, etc., can be backcrossed to the susceptible parent. Plants which are resistant to MYaV can be screened for, and selected for, the presence of one or more of the above SNP markers in order to identify plants comprising a recombinant chromosome 6, comprising a MYaV resistance conferring introgression fragment from the deposited seeds.

Similarly, cultivated melon plants comprising resistance against MYaV, whereby the resistance is conferred by an introgression fragment on chromosome 6, can be generated and/or identified using different methods. For example, to obtain a cultivated melon plant comprising a MYaV-resistance conferring introgression fragment from a wild melon or wild relative of melon, first a wild melon or wild relative of melon is identified which has an MYaV resistance phenotype and/or which comprises one or more of the SNP markers associated with MYaV-resistance disclosed herein, e.g. any one, or more, or all of the markers above. The identified plant is crossed with a susceptible *C. melo* plant to obtain F1 seeds. The F1 hybrid seed and plants grown therefrom, contain one chromosome 6 from the susceptible parent (without QTL MYaV6.1) and one chromosome 6 from the wild MYaV-resistant parent. To generate recombination events between these two homologous chromosomes 6, meiosis needs to take place and plants comprising the recombinant chromosomes 6 need to be identified. For example, the F1 can be selfed to produce F2 plants, and/or resistant F2 plants or F3 plants, etc., can be backcrossed to the susceptible parent. Plants which are resistant to MYaV can be screened for, and/or selected for, the presence of one or more of the above SNP markers and/or screened for, and/or selected for, the presence of the MYaV-resistance phenotype, in order to identify plants comprising a recombinant chromosome 6, comprising a MYaV resistance conferring introgression fragment from the wild melon or wild relative of melon. Alternatively or in addition, QTL mapping can be carried out in order to identify further molecular markers linked to the QTL MYaV6.1 and/or to generate cultivated *C. melo* plants comprising an introgression fragment on chromosome 6 which confers MYaV-resistance.

In one embodiment the presence of the introgression fragment, or the chromosome 6 region (or orthologous chromosome 6 region), comprising the MYaV resistance locus, is detectable by a molecular marker assay which detects at least one of the following markers:

a) the CC or AC genotype for the SNP marker mME15090 in SEQ ID NO: 1 (or SEQ ID NO: 9);

b) the AA or AG genotype for the SNP marker mME12135 in SEQ ID NO: 3 (or SEQ ID NO: 10);

c) any wild melon or wild-relative of melon genome-specific marker in between the marker of a) and b).

In one aspect, at least two, at least three, at least four or more markers are detected from the markers of a), b) or c) above. In one embodiment at least the marker of a) and b) is detected and optionally at least one, two, three or more markers of c) are detected.

Any wild melon or wild-relative of melon genome-specific marker in between the marker of a) and b) refers to any molecular marker which maps genetically to the chromosome 6 region in-between marker mME15090 and mME12135 (see FIG. 1) and/or which lies physically in-between marker mME15090 and mME12135, and which is indicative of the wild melon chromosome 6 region or of the wild-relative of melon chromosome 6 region. This means that the marker is polymorphic between the cultivated melon genome and the wild melon or wild-relative of melon genome. In one aspect, the marker is a Single Nucleotide Polymorphism, but other molecular markers such as RFLP, AFLP, RAPD, DNA sequencing, etc. may equally be used.

In another embodiment the presence of the introgression fragment, or the chromosome 6 region (or orthologous chromosome 6 region), comprising the MYaV resistance locus, is detectable by a molecular marker assay which detects at least one of the following markers:

a) the CC or AC genotype for the SNP marker mME15090 in SEQ ID NO: 1 (or SEQ ID NO: 9);

b) the CC or CT genotype for the SNP marker mME50656 in SEQ ID NO: 7;

c) any wild melon or wild-relative of melon genome-specific marker in between the marker of a) and b).

In one aspect, at least two, at least three, at least four or more markers are detected from the markers of a), b) or c) above. In one embodiment at least the marker of a) and b) is detected and optionally at least one, two, three or more markers of c) are detected.

Any wild melon or wild-relative of melon genome-specific marker in between the marker of a) and b) refers to any molecular marker which maps genetically to the chromosome 6 region in-between marker mME15090 and mME50656 (see FIG. 1) and/or which lies physically in-between marker mME15090 and mME50656, and which is indicative of the wild melon chromosome 6 region or of the wild-relative of melon chromosome 6 region. This means that the marker is polymorphic between the cultivated melon genome and the wild melon or wild-relative of melon genome. In one aspect, the marker is a Single Nucleotide Polymorphism, but other molecular markers such as RFLP, AFLP, RAPD, DNA sequencing, etc. may equally be used.

In one aspect the markers in between marker mME5090 and mME50656 are one or more markers selected from the group: the GG or AG genotype for the SNP marker mME40332 in SEQ ID NO: 2; the AA or AG genotype for the SNP marker mME12135 in SEQ ID NO: 3; the TT or AT genotype for the SNP marker mME28908 in SEQ ID NO: 4; the TT genotype for the SNP marker mME36531 in SEQ ID NO: 5; and the AA or AT genotype for the SNP marker mME9692 in SEQ ID NO: 6.

In yet another embodiment the presence of the introgression fragment, or the chromosome 6 region (or orthologous chromosome 6 region), comprising the MYaV resistance locus, is detectable by a molecular marker assay which detects at least one of the following markers:

a) the AA or AG genotype for the SNP marker mME21377 in SEQ ID NO: 8;

b) the TT or CT genotype for the SNP marker mME13585 in SEQ ID NO: 12.

c) any wild melon or wild-relative of melon genome-specific marker in between the marker of a) and b).

In one aspect, at least two, at least three, at least four or more markers are detected from the markers of a), b) or c) above. In one embodiment at least the marker of a) and b) is detected and optionally at least one, two, three or more markers of c) are detected.

Any wild melon or wild-relative of melon genome-specific marker in between the marker of a) and b) refers to any molecular marker which maps genetically to the chromosome 6 region in-between marker mME21377 and mME13585 (see FIG. 1) and/or which lies physically in-between marker mME21377 and mME13585, and which is indicative of the wild melon chromosome 6 region or of the wild-relative of melon chromosome 6 region. This means that the marker is polymorphic between the cultivated melon genome and the wild melon or wild-relative of melon genome. In one aspect, the marker is a Single Nucleotide Polymorphism, but other molecular markers such as RFLP, AFLP, RAPD, CASP markers, DNA sequencing, etc. may equally be used.

In one aspect the markers in between marker mME21377 and mME13585 are one or more markers selected from the group: the CC or AC genotype for the SNP marker mME15090 in SEQ ID NO: 9; the AA or AG genotype for the SNP marker mME12135 in SEQ ID NO: 10; and the TT or GT genotype for the SNP marker mME36533 in SEQ ID NO: 11.

The molecular markers described herein may be detected according to standard method. For example SNP markers can easily be detected using a KASP-assay (see www.kp-bioscience.co.uk) or other assays. A KASP-assay has been developed for a number of SNPs in Example 3. For developing the KASP-assay 70 base pairs upstream and 70 basepairs downstream of the SNP were selected and two allele-specific forward primers and one allele specific reverse primer was designed. See e.g. Allen et al. 2011, Plant Biotechnology J. 9, 1086-1099, especially p 097-1098 for KASP assay method.

Thus, in one aspect, the SNP markers and the presence/absence of the marker associated with the MYaV-resistance allele is determined using a KASP assay, but equally other assays can be used. For example, optionally DNA sequencing may also be used.

Physical mapping using BACs (Bacterial Artificial Chromosomes) and development of markers for the BACs can be carried out to map the physical location of MYaV6.1 on chromosome 6 and to develop markers which lie physically between any of the markers mentioned and to determine physical distances between markers and/or determine introgression size.

The size of an introgression fragment can for example also be determined by visualization of the introgression using Fluorescent in situ hybridization (FISH) images (Verlaan et al. 2011, Plant Journal 68: 1093-1103).

In one embodiment of the invention, the MYaV-resistance conferring introgression fragment is equal to or less than 10 Mb in size, preferably equal to or less than 8 Mb in size, equal to or less than 7, 6, 5, 4, 3, 2 or 1 Mb in size, more preferably even less, such as equal to or less than 500 kb, 400 kb, 300 kb, 200 kb, 100 kb, 50 kb, 25 kb, 20 kb, 15 kb, or less, but still comprises the MYaV-resistance allele and still confers MYaV resistance to an otherwise susceptible *C. melo* plant. Resistance is conferred by the recombinant chromosome 6, and the introgression fragment comprising the MYaV allele when the introgression fragment is in heterozygous or homozygous form. Plants with smaller introgression fragments on chromosome 6 can be generated by generating new recombinant plants from a population of plants derived from a cross between a cultivated MYaV susceptible plant and a wild MYaV resistant melon or relative of melon. Alternatively, when a cultivated *C. melo* plant having a MYaV-resistance conferring introgression fragment is identified, the introgression size can be reduced by e.g. selfing that plant and selecting recombinant progeny having smaller introgression sizes.

In tomato, for example the large *S. chilense* introgression fragment on chromosome 6 (about 27 cM) which comprises the Ty-3 allele has been reduced by selecting a recombinant progeny line (LA1931-AL-F2), which comprises a much smaller *S. chilense* introgression fragment (about 6 cM) comprising Ty-3 (see Ji et al. 2007, Mol. Breeding 20: 271-284).

The cultivated melon plant according to the invention may be an inbred or an F1 hybrid. In one aspect the F1 hybrid comprises the introgression fragment in heterozygous form, i.e. produced by crossing two inbred parent lines, one of which possesses the introgression fragment (preferably in homozygous form, although not necessarily) and collecting the F1 hybrid seeds from said cross. The F1 hybrid may also comprise the introgression fragment in homozygous form, i.e. produced by crossing two inbred parent lines, each comprising the introgression fragment in homozygous or heterozygous form.

The cultivated melon plant may be of any type. Preferably it has good agronomic and good fruit quality characteristics, such as large average fruit size (at least 500 g, 600 g, 700 g, 800 g, 900 g, 1000 g or more), high average brix of the fruits (e.g. an average refractometer % total soluble solids of at least 10%, 12%, 14%, 16%, 18% or more), many fruits being produced per plant, firm fruit flesh, etc. The cultivated melon may be a *C. melo cantalupensis, C. melo inodorous* and *C. melo reticulatus*. *C. melo cantalupensis* are also referred to as Canteloupes and are primarily round in shape with prominent ribs and almost no netting. Most have orange, sweet flesh and they are usually very fragrant. In contrast to the European cantaloupe, the North American 'Cantaloupe' is not of this type, but belongs to the true muskmelons. *C. melo inodorous* (or winter melons) can be subdivided into different types, such as Honeydew melon, Piel de Sapo, Sugar melon, Japanese melon, etc. *C. melo reticulatus* is the true muskmelon, with reticulated skin (netted) and includes Galia melons, Sharlyn melons and the North American cantaloupe. Melons come in many sizes and shapes including round, oval, and cylindrical. The flesh is generally orange and quite sweet, but some varieties of melon and specifically, the Persian melons, can have green or white flesh. Some green-fleshed melons are quite sweet, but most of the green- and white-fleshed melons have a less sweet, but very refreshing flavor.

Also other resistances may be introduced into the melon plants of the invention, such as resistance to one or more of the following diseases: Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum* f. sp. *melonis* (Fom) race 0, *Fusarium oxysporum* f. sp. *melonis* (Fom) race 1, *Fusarium oxysporum* f. sp. *melonis* (Fom) race 2, *Fusarium oxysporum* f. sp. *melonis* (Fom) race 1.2, *Fusarium* Wilt R2, Root Knot (Nematode), Anthracnose, Cucumber Mosiac, and Squash Mosaic, and/or resistance to one or more of the following pests: Aphid resistance, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer. Other resistance genes, against pathogenic viruses, fungi, bacteria or pests may also be introduced.

In one aspect seeds from which plants of the invention can be grown are provided. In one aspect the seeds are F1 hybrid seeds, which comprise the recombinant chromosome 6 in homozygous or heterozygous form and which have an MYaV-resistance phenotype when grown in the field.

Also containers and packages containing or comprising seeds from which plants of the invention can be grown are provided herein. These may be labelled as containing cultivated melon seeds having MYaV resistance.

Also progeny seeds and progeny plants of plants of the invention are provided, which retain the MYaV resistance conferring introgression on chromosome 6, or a smaller introgression, i.e. a resistance conferring part of the introgression fragment. Progeny may be any generation obtained by selfing a melon plant according to the invention and/or crossing a melon plant according to the invention with another melon plant one or more times. Progeny are, therefore, either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another melon plant (and/or with a wild relative of melon). Progeny are preferably selected to retain the recombinant chromosome 6 comprising the introgression fragment from wild melon or from a wild relative of melon. Thus progeny also have the MYaV-resistance phenotype, preferably the same level of MYaV resistance as the plant used in the initial cross or selfing. The presence of (or retention of) the introgression fragment comprising the QTL MYaV6.1 can be determined in the MYaV-resistance assay, phenotypically, and/or the molecular marker assay(s) described herein. Regarding phenotypic assessment, of course consideration needs to be given to the dominance nature of the MYaV-allele.

In a further aspect parts of the melon plants according to the invention are provided. Parts include for example cells and cell-cultures, tissue cultures, vegetative plant tissues (leaves, roots, etc.), flowers, pollen, embryos, fruits, parts of fruits, etc. The plant parts comprise the introgression fragment on chromosome 6, as described, and as can be detected using one or more of the MYaV-marker assays described. Also, when whole plants are regenerated from such melon parts, such as cells, cell- or tissue cultures, the regenerated plants comprise the recombinant chromosome 6, and the MYaV resistance phenotype.

Thus, also provided is a plant cell, tissue or plant part of a plant or of a seed according the invention comprising at least one recombinant chromosome 6, wherein said recombinant chromosome 6 comprises an introgression fragment from a wild C. melo plant and wherein said introgression fragment comprises an allele conferring MYaV resistance.

Also in vitro cell cultures and in vitro tissue cultures are encompassed herein, of cells or tissues comprising a recombinant chromosome 6 described. Preferably the cells or tissues can be regenerated into a whole melon plant, i.e. the cells are regenerable cells and the tissues comprise regenerable cells. Thus, also vegetative propagations of the plants according to the invention are an embodiment herein. Thus, a vegetatively propagated cultivated melon plant is provided which comprises the MYaV resistance phenotype and a recombinant chromosome 6 as described herein.

In a specific aspect a melon fruit harvested from a plant according to the invention is provided. Marketable melon fruits are generally sorted by size and quality after harvest. Also containers or packages comprising or consisting of harvested melon fruits are provided. Again, the cells of the fruits are distinguishable from other melons by the presence of the recombinant chromosome 6 (as determinable in one or more of the molecular marker assays and/or in an MYaV-resistance assay by e.g. growing the seeds present in the fruits, or progeny obtained by selfing the plants grown from the seeds).

The invention also provides for a food or feed product comprising or consisting of a plant part described herein preferably a melon fruit or part thereof and/or an extract from a plant part described herein. The food or feed product may be fresh or processed, e.g., canned, steamed, boiled, fried, blanched and/or frozen, etc. For example, containers such as cans, boxes, crates, bags, cartons, Modified Atmosphere Packagings, films (e.g. biodegradable films), etc. comprising plant parts such as fruits or fruit parts (fresh and/or processed) described herein are also provided herein.

Methods and Uses According to the Invention

In a further embodiment, the invention provides for a method of producing a new cultivated melon plant which comprises an introgression fragment which confers MYaV-resistance when in homozygous form, as described. The method comprises crossing a plant of the invention, or a progeny plant thereof, either as male or as female parent, with a second melon plant (or a wild relative of melon) one or more times, and/or selfing a melon plant according to the invention, or a progeny plant thereof, one or more times, and selecting progeny from said crossing and/or selfing. The first and/or the second melon plant may for example be a line or variety of the species C. melo cantalupensis, C. melo inodorous or C. melo reticulatus.

Thus, a method for transferring the recombinant chromosome 6, comprising the MYaV-resistance conferring locus (MYaV6.1), from one (cultivated) melon plant into another (cultivated) melon plant is provided, especially into MYaV-susceptible varieties or breeding lines.

The method comprises the steps of:
a) providing a first melon plant comprising at least one recombinant chromosome 6 having an introgression fragment comprising an allele conferring MYaV resistance in homozygous form,
b) providing a second melon plant, especially a MYaV susceptible melon plant,
c) crossing said melon plant of a) with said melon plant of b),
d) collecting F1 hybrid seeds from said cross and optionally
e) selfing the plant grown from said F1 hybrid seeds to produce F2 seeds, and optionally selecting the F2 seeds having the recombinant chromosome 6, and optionally
f) breeding further with plants grown from said F2 seeds to produce a melon plant having good agronomic characteristics and comprising the introgression fragment in homozygous or heterozygous form.

The presence or absence of the recombinant chromosome 6, and of the introgression fragment, may be determined by one or more of the molecular marker assays described herein and/or by MYaV-resistance assays. Further breeding in step f) may comprise selfing, crossing, double haploid production, backcrossing, etc. Plants and seeds obtainable by the above method are encompassed herein.

Also provided is a method of producing C. melo F1 hybrid plants comprising a MYaV resistance phenotype comprising:
a) providing a first inbred melon plant comprising at least one recombinant chromosome 6 having an introgression fragment comprising an allele conferring MYaV resistance,
b) providing a second inbred melon plant with or without recombinant chromosome 6 having an introgression fragment comprising an allele conferring MYaV resistance,
c) crossing said melon plant of a) with said melon plant of b),
d) collecting F1 hybrid seeds from said cross.

The inbred melon plant of a) and b) may be homozygous and/or heterozygous for the introgression fragment, and they may contain introgression fragments of different sizes and/or of different origin, i.e. from different wild melons or wild relatives of melon.

The F1 hybrid seeds preferably comprise at least one recombinant chromosome 6 and the F1 plants grown from the seeds are therefore MYaV resistant in their phenotype.

The presence or absence of the recombinant chromosome 6, and of the introgression fragment, may be determined by one or more of the molecular marker assays described herein and/or by MYaV-resistance assays. Plants and seeds obtainable by the above method are encompassed herein.

In a different aspect a method for producing a cultivated *C. melo* plant comprising an introgression fragment on chromosome 6, wherein said introgression fragment comprises an MYaV-resistance allele, is provided, said method comprising the steps:

a) providing a first cultivated melon plant being susceptible to MYaV, b) providing a second wild melon plant being resistance to MYaV, c) crossing said melon plant of a) with said melon plant of b), d) collecting F1 seeds from said cross and backcrossing an F1 plant to the melon plant of a) to produce a backcross (BC1) population, or selfing said F1 plants one or more times to produce an F2 or F3 or higher generation selfing population, e) optionally backcrossing a plant of d) one or more times to the melon plant of a) to produce a higher generation backcross population, and f) identifying a F2, F3, or higher generation selfing, or BC1 or higher generation backcross plant which comprises an introgression on chromosome 6, wherein said introgression fragment comprises an MYaV-resistance allele.

When referring to backcross populations in the method, the backcross populations may also be selfed, i.e. BC1S1, BC1S2, BC2S1, BC2S2, or others.

In one or more of steps b) to f) the presence of the MYaV-resistance allele (or the introgression fragment or wild chromosome 6 region comprising the allele) may be tested (and plants may be selected) by carrying out a molecular marker assay as described elsewhere herein, e.g. by determining whether the plant comprises the CC or AC genotype for the SNP marker mME15090 in SEQ ID NO: 1 and the AA or AG genotype for the SNP marker mME12135 in SEQ ID NO: 3 or any wild melon or wild-relative of melon genome-specific marker in between the marker mME15090 and mME12135.

Using this method, one can generate and/or select new cultivated melon plants comprising an introgression with QTL MYaV6.1 from a wild source, such as a wild melon or wild relative of melon (such as from NCIMB 41966 or NCIMB 41969, or other wild melons or wild relatives of melon).

In one aspect the method for producing a cultivated *C. melo* plant comprising an introgression fragment on chromosome 6, wherein said introgression fragment comprises an MYaV-resistance allele, comprises the steps:

a) providing a first cultivated melon plant being susceptible to MYaV, b) providing a second wild melon plant being resistance to MYaV, c) crossing said melon plant of a) with said melon plant of b), d) collecting F1 seeds from said cross and backcrossing an F1 plant to the melon plant of a) to produce a backcross (BC1) population, or selfing said F1 plants one or more times to produce an F2 or F3 population, e) optionally selfing the backcross population to produce e.g. a BC1S1 or BC1S2 population, f) identifying a F2, F3, BC1 BC1S1, or BC1S2 plant which comprises the CC or AC genotype for the SNP marker mME15090 in SEQ ID NO: 1 and the AA or AG genotype for the SNP marker mME12135 in SEQ ID NO: 3 or any wild melon or wild-relative of melon genome-specific marker in between the marker mME15090 and mME12135.

Also provided is a method for identifying a wild melon plant comprising MYaV resistance on chromosome 6, said method comprising:

a) providing a wild melon accession or several wild melon accessions;

b) screening said wild melon accession(s) using a molecular marker assay which detects at least one SNP marker selected from the group consisting of: SNP marker mME15090 in SEQ ID NO: 1 and SNP marker mME12135 in SEQ ID NO: 3; and c) identifying and/or selecting a wild melon plant comprising at least the CC or AC genotype for the SNP marker mME15090 in SEQ ID NO: 1 and the AA or AG genotype for the SNP marker mME12135 in SEQ ID NO: 3 or any wild melon or wild-relative of melon genome-specific marker in between the marker mME15090 and mME12135; and optionally d) confirming MYaV resistance in an MYaV resistance assay; and optionally e) introgressing said MYaV resistance from said wild accession into cultivated melon.

In step c) also other molecular marker tests described elsewhere herein can be used. With this method one can, thus, screen wild melon accessions or wild relatives of melon for the presence of one or more of the markers and, thus, the presence of QTL MYaV6.1 and introgress the resistance-conferring part of these new resistance sources into cultivated, MYaV-susceptible, melon plants. Plants and seeds obtained by this method are also an embodiment of the invention.

In still another aspect a method for identifying a cultivated *C. melo* plant comprising an introgression fragment on chromosome 6, wherein said introgression fragment comprises an MYaV-resistance allele, is provided, said method comprising:

a) providing a population of recombinant, cultivated *C. melo* plants (such as an F2, F3, or higher generation selfing, BC1, BC2, BC1 S1 or higher generation backcross population), b) screening said population using a molecular marker assay which detects at least one SNP marker selected from the group consisting of:

SNP marker mME15090 in SEQ ID NO: 1 and SNP marker mME12135 in SEQ ID NO: 3 or any wild melon or wild-relative of melon genome-specific marker in between the marker mME15090 and mME12135; and c) identifying and/or selecting a plant comprising at least the CC or AC genotype for the SNP marker mME15090 in SEQ ID NO: 1 and the AA or AG genotype for the SNP marker mME12135 in SEQ ID NO: 3 or any wild melon or wild-relative of melon genome-specific marker in between the marker mME15090 and mME12135.

In this method also other molecular marker tests described elsewhere herein can be used. Thus, using this method one can detect the presence of an introgression fragment on chromosome 6 comprising QTL MYaV6.1 in cultivated melon plants or plant parts.

In yet another aspect a method for detecting whether a cultivated *C. melo* plant comprises an introgression fragment on chromosome 6, wherein said introgression fragment comprises an MYaV-resistance allele, is provided, said method comprising:

a) providing cultivated *C. melo* plant, b) screening said plant using a molecular marker assay which detects at least one SNP marker selected from the group consisting of:

SNP marker mME15090 in SEQ ID NO: 1 and SNP marker mME12135 in SEQ ID NO: 3 or any wild melon or wild-relative of melon genome-specific marker in between the marker mME15090 and mME12135.

Molecular marker screening obviously involves obtaining plant material and analyzing the genomic DNA of the material for the marker genotype.

In this method also other molecular marker tests described elsewhere herein can be used. Thus, using this method one can detect the presence of an introgression fragment on chromosome 6 comprising QTL MYaV6.1 in cultivated melon plants or plant parts. If one or more of the markers which are linked to the QTL are present, one can conclude that the plant comprises a MYaV-resistance conferring introgression fragment on chromosome 6.

One can also use the methods and the markers described herein to reduce the size of the wild introgression fragment comprising the QTL MYaV6.1, i.e. to generate and select recombinants having a smaller introgression fragment on chromosome 6, but which retain the MYaV resistance conferring part of the introgression fragment. One can equally develop alternative molecular markers linked to MYaV6.1 for use in any of the aforementioned methods.

In one aspect the invention encompasses the use of a recombinant chromosome 6 comprising an introgression fragment from a wild *C. melo* plant, said introgression fragment comprising an allele conferring MYaV-resistance, for breeding melon varieties having MYaV resistance.

In one aspect the invention encompasses the use of a recombinant chromosome 6 comprising an introgression fragment from a wild *C. melo* plant, said introgression fragment comprising an allele conferring MYaV-resistance, for breeding melon varieties having MYaV resistance, wherein said recombinant chromosomes 6 is the recombinant chromosome 6 as found in seeds deposited under accession number NCIMB 42113 or NCIMB 42198, or is derived from said recombinant chromosome 6. Thus, in one aspect a cultivated melon plant according to the invention comprising a recombinant chromosome 6 obtained by (obtainable by) crossing a plant grown from seeds deposited under accession number NCIMB 42113, or NCIMB 42198, or from progeny thereof which retain the recombinant chromosome 6, with another melon plant.

In one aspect, the plants, cells, tissues and plant parts according to the invention do not comprise the introgression fragment from PI313970, which introgression fragment comprises a CYSDV resistance QTL linked to at least one marker located on the chromosome equivalent to linkage group (LG) 6 of melon accession PI313970 as described and claimed in EP1962578B1. As mentioned, in EP1962578B1 arbitrarily named LG6 is ICuGI LG VI of melon, but corresponds to ICuGI Linkage Group V (LG V). In one aspect the cultivated melon plants according to the invention comprises a chromosome 5 (ICuGI LG V) and said chromosome 5 does not comprises the introgression from PI313970, which introgression comprises a CYSDV resistance QTL linked to at least one marker located on the chromosome equivalent to linkage group (LG) 6 of melon accession PI313970 as described and claimed in EP1962578B1.

In another aspect, a cultivated melon plant comprising a recombinant chromosome 6 according to the invention and further comprising a recombinant chromosome 5 which comprises an introgression from PI313970, which introgression comprises a CYSDV resistance QTL linked to at least one marker located on the chromosome equivalent to linkage group (LG) 6 of melon accession PI313970 as described and claimed in EP1962578B1 is encompassed herein, i.e. a cultivated melon plant, parts and cells thereof, comprising at least two introgression fragments from wild melon, one conferring MYaV resistance on chromosome 6 (as described throughout the specification) and one conferring CYSDV resistance on chromosome 5 (ICuGI LG V).

DNA and Chromosomes According to the Invention

In one aspect a modified (recombinant) cultivated *C. melo* chromosome 6 is provided herein, which comprises an introgression fragment of a wild melon or wild relative of melon, as described throughout the specification. In one aspect the recombinant chromosome 6 is isolated from its natural environment. In another aspect it is in a plant cell, especially in a melon cell, especially in a cultivated *C. melo* cell. Also an isolated part of the recombinant chromosome 6 comprising the MYaV-allele is provided herein.

In a further aspect a recombinant nucleic acid molecule, especially a recombinant DNA molecule, is provided which comprises a MYaV-allele according to the invention. In one aspect the MYaV-allele is detectable by one or more of the molecular marker assays described herein. Also a DNA vector is provided comprising the recombinant DNA. The recombinant DNA molecule or DNA vector may be an isolated nucleic acid molecule. The DNA comprising the MYaV-allele may be in a microorganisms, such as a bacterium (e.g. *Agrobacterium*).

The use of such a (isolated or extracted) nucleic acid molecule and/or of such a recombinant chromosome 6 or part thereof for generating plant cells and plants comprising a MYaV allele is encompassed herein. In one aspect it may be used to generate transgenic melon cells, melon plants and melon parts (e.g. fruits) comprising the MYaV allele and the plant comprises an MYaV resistance phenotype.

Thus, transgenic plant cells, e.g. transgenic melon cells, comprising in their genome a recombinant chromosome 6 as described and/or a recombinant nucleic acid molecule comprising a MYaV-allele are also an embodiment of the invention. In one aspect the DNA molecule comprising the MYaV-allele is stably integrated into the melon genome.

The MYaV allele may also be cloned and a chimeric gene may be made, e.g. operably linking a plant expressible promoter to the MYaV allele. Such a chimeric gene may be introduced into a plant cell and the plant cell may be regenerated into a whole plant to produce a transgenic plant. In one aspect the transgenic plant is a melon plant.

Thus, transgenic plants, especially transgenic cultivated melon plants, comprising an MYaV resistance allele and having an MYaV resistance phenotype are provided herein.

Especially cells or cell cultures comprising a recombinant chromosome 6 according to the invention are an embodiment, independent whether the recombinant chromosome 6 is introduced by transgenic methods or by breeding methods. The cells are e.g. in vitro and are regenerable into melon plants comprising the recombinant chromosome 6 of the invention.

Also the molecular marker sequences (and isolated nucleic acid molecules comprising the sequence) disclosed herein and molecular markers in between any of the mentioned molecular markers described herein and depicted in FIG. 1, linked to the MYaV-resistance conferring QTL, and their use in detecting and/or generating MYaV resistant melon plants are encompassed herein.

FIGURE LEGENDS

FIG. 1: The LOD profile of MYaV6.1, a QTL on melon linkage group VI (LGVI) conferring resistance to MYaV.

The linkage maps of LGVI for the two crosses [(990631-2)-Q-1-K×NCIMB41966 and Amaregal×NCIMB41969] are represented by solid bars, and SNP markers and distances in cM (centiMorgan) are to the right and left sides of the bars, respectively. Common SNP markers between the two maps are indicated with connecting lines. The LOD profile on the (990631-2)-Q-1-K×NCIMB41966 map shows results of field evaluations of replicated F3 families in 2010 while that of Amaregal×NCIMB41969 shows 2011 results of field evaluations of F2 plants. The peak LOD for the cross (990631-2)-Q-1-K×NCIMB41966 was 6.3, explaining 32.6% of observed variation in 2010. The peak LOD of the cross Amaregal×NCIMB41969 was 50.3, explaining 91.7% of observed variation in 2011.

FIG. 2: Photograph taken in Brazil of susceptible melon variety Hibrix (middle row) showing MYaV symptoms. The rectangle shows the part of the melon plant that is phenotyped for symptoms.

SEED DEPOSITS

A representative sample of seeds of wild melon accessions comprising the QTL (designated MYaV6.1) for MYaV resistance on chromosome 6 were deposited by Nunhems B.V. on 2 May 2012 at the NCNB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 41966 and NCIMB 41969.

A representative sample (2600) of seeds (BC1S2) of a cultivated melon plant comprising the QTL for MYaV resistance on chromosome 6 in homozygous form (designated MYaV6.1) was deposited by Nunhems B.V. on 15 Feb. 2013 at the NCIMB Ltd. (Ferguson Building, Craibstone Estate, Bucksburn Aberdeen, Scotland. AB21 9YA, UK) according to the Budapest Treaty, under the Expert Solution (EPC 2000, Rule 32(1)). Seeds were given the following deposit number: NCIMB 42113.

A representative sample of (1300) of seeds (BC4F2) of a cultivated melon plant comprising the QTL for MYaV resistance on chromosome 6 in homozygous form (designated MYaV6.1) was deposited by Nunhems B.V. on 12 Dec. 2013 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit number: NCIMB 42198.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The following non-limiting Examples describe how one can obtain plants according to the invention, comprising a recombinant chromosome 6. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard breeding methods are described in 'Principles of Plant breeding', Second Edition, Robert W. Allard (ISBN 0-471-02309-4).

EXAMPLE 1

Resistance on Chromosome 6 of NCIMB 41966

1.1 Material and Methods 1.1.1 F2 and F3 Population Development

A cross was made between the breeding line (990631-2)-Q-1-K, which is susceptible to MYaV, and a wild melon accession, *Cucimis melo* ssp. *agrestis*, obtained from the USA but originally originating from India, seeds of which were deposited by Nunhems B.V. under accession number NCIMB 41966.

F1 progeny obtained from the cross were selfed to obtain an F2 population, which was used for genotyping (96 F2 plants were genotyped). F2 plants were selfed to obtain F3 families, which were phenotyped in an MYaV resistance assay in the field, near Mossoro, Brazil in 2010, as described below.

1.1.2 MYaV-resistance Assay of F3 Families

The MYaV-resistance assays were conducted in 2010 in the open field near Mossoro, under natural high MYaV incidence. Each F3 family was planted in three replicates of 20 plants per replicate in 2010, together with susceptible controls (4 plants, 3 replicates) and resistant control NCIMB41966 (20 plants). A complete randomized design was used, as the disease pressure was uniform across the field.

Susceptible controls were Glory F1 (Origene Seeds), Ruidera F1, Amaregal F1, Guapore, Goldex, DRY9150 and Sancho (Syngenta).

Phenotyping for MYaV-symptoms was conducted visually, when the susceptible controls showed clear yellowing symptoms.

Each plant was given a disease score on the following scale, whereby only the older leaves, i.e. the first third (⅓$^{rd}$) of the plant around the main stem and root system, are used. Thus, when referring herein to "all leaves" or "few leaves" or a certain percentage of total leaf area, only the leaves in the oldest ⅓$^{rd}$ of the plant is referred to, see also FIG. 2 where the black rectangle indicates the ⅓$^{rd}$ of the plant that is scored according to the following scale:

| | |
|---|---|
| 9 | Totally green (all leaves in the oldest $\frac{1}{3}^{rd}$ of the plant are green) |
| 8 | Few leaves (in the oldest $\frac{1}{3}^{rd}$ of a plant) start to show yellow shadow/mottling |
| 7 | Up to about 17% of total leaf area (in the oldest $\frac{1}{3}^{rd}$ of a plant) is yellow |
| 6 | About 17% to 32% of total leaf area (in the oldest $\frac{1}{3}^{rd}$ of a plant) is yellow |
| 5 | 33% to 48% of total leaf area (in the oldest $\frac{1}{3}^{rd}$ of a plant) is yellow |
| 4 | 49% to 64% of total leaf area (in the oldest $\frac{1}{3}^{rd}$ of a plant) is yellow |
| 3 | 65% to 80% of total leaf area (in the oldest $\frac{1}{3}^{rd}$ of a plant) is yellow |
| 2 | 81% to 99% leaves area (in the oldest $\frac{1}{3}^{rd}$ of the plant) yellow |
| 1 | Totally yellow (all leaves in the oldest $\frac{1}{3}^{rd}$ of the plant are yellow) |

The average disease score was calculated per F3 family and per control.

1.1.3 Genotyping of F2 Families

Genotyping of F2 families was done using the SNP (Single Nucleotide Polymorphism) Illumina Infinium Array, containing 4600 SNPs. Some ICuGI SSR (Single Sequence Repeat) markers were also analysed and served as anchor markers alongside a few other anchor SNP markers to determine linkage group number and orientation.

1.1.4 Data Analysis of F2 Genotype and F3 Phenotype Data

Linkage mapping was conducted using JoinMap v4 and QTL analysis was conducted with MapQTL v5 software.

1.2 Results 1.2.1 Results of the MYaV Resistance Assay in 2010

The results for the susceptible and resistant checks are shown below:

| | Average Yellowing Scoring |
|---|---|
| MYaV susceptible check varieties | |
| Glory | 2 |
| Ruidera | 1.44 |
| Amaregal | 1.29 |
| Guaporé | 1 |
| Goldex | 1 |
| DRY 9150 | 1 |
| Sancho | 1 |
| MYaV resistant check | |
| NCIMB41966 | 9 |

1.2.2 Results of QTL Mapping of F2 and F3 Families

The SNP markers mapped to 12 linkage groups, corresponding to the haploid chromosome number of melon.

For the 2010 phenotype data a significant QTL for MYaV resistance was found on linkage group VI (based on ICuGI nomenclature), with a peak LOD score of 6.3 and explaining 32.6% of the observed phenotypic variation for MYaV resistance.

The results are shown in FIG. 1.

The following SNP markers were associated with the MYaV resistance phenotype. The genotype of the resistant and susceptible parent at the marker locus is also indicated in the Table.

TABLE 1

| NMID | SNP | Susceptible parent: (990631-2)- Q-1-K | Resistant parent NCIMB 41966 | LOD score (2010 data) | SEQ ID NO: |
|---|---|---|---|---|---|
| mME15090 | [A/C] | AA | CC | 1.33** | 1 |
| mME40332 | [A/G] | AA | GG | 2.20** | 2 |
| mME12135 | [A/G] | GG | AA | 5.30 | 3 |
| mME28908 | [A/T] | AA | TT | 5.26 | 4 |
| mME36531 | [C/T] | TC | TT | 3.44 | 5 |
| mME9692 | [A/T] | TT | AA | 3.13 | 6 |
| mME50656* | [C/T] | TT | CC | 1.43** | 7 |

*corresponds to EST marker A_38-F04 (GenBank Accession AM730270), which was used to link the genetic map of linkage group VI to the physical map (scaffold 00021). See Garcia-Mas et al. June 2012, PNAS Early Edition, page 1-6, Supplementary Information Appendix - FIG. S2.
**even though the LOD score is below 3.0, these markers are still considered significant, as confirmed using separate phenotyping data obtained in 2009 (results not shown)

EXAMPLE 2

Resistance on Chromosome 6 of NCIMB 41969

2.1 Material and Methods 2.1.1 F2 Population Development

A cross was made between the hybrid Galia melon variety Amaregal F1, which is susceptible to MYaV, and a wild melon accession, obtained from Spain but originally originating from Uzbekistan, seeds of which were deposited by Nunhems B.V. under accession number NCIMB 41969.

F1 progeny obtained from the cross were selfed to obtain an F2 population, which was used for genotyping (181 F2 plants). F2 plants were phenotyped in an MYaV resistance assay in the field, near Mossoro, Brazil in 2011, as described below.

2.1.2 MYaV-resistance Assay of F2 Plants

The MYaV-resistance assays were conducted in 2011 in the open field near Mossoro, under natural high MYaV incidence.

Susceptible controls (10 plants per plot) were Amaregal (Nunhems), Sancho (Syngenta), and Caribbean Gold. Also NCIMB 41969 was included as resistant check (20 plants per plot).

Phenotyping for MYaV-symptoms was conducted visually, when the susceptible controls showed clear yellowing symptoms.

Each plant was given a disease score on the scale described above under 1.1.2.

The average disease score was calculated per plant line or variety.

2.1.3 Genotyping of F2 Families

Genotyping of F2 plants was done using a genome wide set of 96 markers on a KASP-platform for the initial scaffold map. Some ICuGI SSR (Single Sequence Repeat) markers were also analysed and served as anchor markers alongside a few other anchor SNP markers to determine linkage group number and orientation.

2.1.4 Data Analysis of F2 Genotype and F2 Phenotype Data

Linkage mapping was conducted using JoinMap v4 and QTL analysis was conducted with MapQTL v5 software.

2.2 Results

2.2.1 Results of the MYaV Resistance Assay in 2011

The results for the susceptible and resistant checks are shown below:

|  | Average Yellowing Scoring |
|---|---|
| MYaV susceptible check varieties | |
| Amaregal | 1 |
| Sancho | 1 |
| Caribbean Gold | 1 |
| MYaV resistant check | |
| NCIMB41969 | 9 |

2.2.2 Results of QTL Mapping of F2 Plants

The SNP markers mapped to 12 linkage groups, corresponding to the haploid chromosome number of melon.

A significant QTL for MYaV resistance was found on linkage group VI (based on ICuGI nomenclature), with a peak LOD score of 50.3 and explaining 91.7% of the observed phenotypic variation for MYaV resistance.

The results are shown in FIG. 1.

The following SNP markers were associated with the QTL. The genotype of the resistant and susceptible parent at the marker locus is also indicated in the Table.

TABLE 2

| NMID | SNP | Susceptible parent: | Resistant parent NCIMB 41969 | LOD score (2011 data) | SEQ ID NO: |
|---|---|---|---|---|---|
| mME21377 | [A/G] | GG | AA | 6.81 | 8 |
| mME15090 | [A/C] | AA | CC | 17.14 | 9 |
| mME12135 | [A/G] | GG | AA | 24.86 | 10 |
| mME36533 | [G/T] | GG | TT | 7.64 | 11 |
| mME13585 | [C/T] | CC | TT | 6.58 | 12 |

Examples 1 and 2, above, show that an introgression fragment from wild melons, comprising a MYV resistance conferring Locus, confers MYaV-resistance when transferred into cultivated melon. As the QTL mapped to linkage group 6, the QTL was termed MYaV6.1. Seeds of such cultivated melon plants comprising the QTL termed MYaV6.1, have been deposited under deposit number NCIMB 42113 (comprising the introgression fragment from NCIMB 41969) and NCIMB 42198 (comprising the introgression fragment from NCIMB 41966).

The QTL MYaV6.1 was found in two wild melon accessions, from different origins (India and Uzbekistan), and two SNP markers (mME12135 and ME15090) was found to be commonly linked to the QTL in both populations, while five SNP markers (mME40332, mME28908, mME36531, mME9692 and mME50656) and three SNP markers (mME21377, mME36533 and mME13585) were associated with (linked to) the QTL derived from NCIMB41966 and NCIMB41969, respectively.

One or more (at least two, three, four, five, six, seven, or more) or all of the SNP markers associated with MYaV6.1 provided herein, can be used for various purposes, such as a) to detect the presence of an introgression fragment on chromosome 6 comprising QTL MYaV6.1 in cultivated melon plants or plant parts;

b) to transfer the recombinant chromosome 6, comprising the MYaV-resistance conferring locus (MYaV6.1), from one cultivated melon into other cultivated melon plants, especially MYaV-susceptible varieties or breeding lines;

c) to generate and/or select new cultivated melon plants comprising an introgression with QTL MYaV6.1 from a wild source, such as a wild melon or wild relative of melon (such as from NCIMB 41966 or NCIMB 41969, or other wild melons or wild relatives of melon), d) to reduce the size of the wild introgression fragment comprising the QTL MYaV6.1, i.e. to generate and select recombinants having a smaller introgression fragment on chromosome 6, but which retain the MYaV resistance conferring part of the introgression fragment;

e) to develop alternative molecular markers for any of the aforementioned purposes, linked to MYaV6.1;

f) to screen wild melon accessions or wild relatives of melon for the presence of one or more of the markers and, thus, the presence of QTL MYaV6.1 and to introgress the resistance-conferring part of these new resistance sources into cultivated, MYaV-susceptible, melon plants.

EXAMPLE 3

SNP Assays (KASP Assay) or "MYaV-marker Assay"

In order to screen plants for the presence of one or more of the above molecular markers, linked to the introgression fragment conferring MYaV resistance, a KASP-assay (a SNP genotyping assay or KBioscience Allele-Specific PCR genotyping-assay) was developed for SNP markers mME21377, mME1590, mME12135, mME36533, mME13585 and mME36531.

Based on the genomic sequences comprising the SNP (see Table 3 below and Sequence listing), for each SNP marker two allele-specific forward primers (i.e. detecting either the nucleotide of the susceptible or resistant parent at the SNP locus) and one common reverse primer (in italics) were developed, indicated in Table 3 and 4 (all sequences are given in 5' to 3'-direction).

TABLE 3

| marker | SNP | Genomic sequence for primer design (5' to 3' direction) |
|---|---|---|
| mME12 135 | [A/ G] | TGCCAGCCGCACGTTTCATCTTTTGGTAATAACTATTAAAAGCAT*AGGA* *AGCATGTGCTTGAAGGGAGTT*[A/G]GGATCGTAACAAGCGCCACCCTGTT GAATGGAACGGCAATCAGCCTGTCCTTCACCACAAGCATAGTCCA [SEQ ID NO: 3 and SEQ ID NO: 10] |
| mME36 531 | [C/ T] | CTGTTGAAATATATTATGCCGTTATTTTCTTGGAATATTTGCTGT*CAAAT* *CCTGTGTTATTGACTGGTCT*[C/T]*TTTTGTTAGGTCTACGCTGAAGGACC*A GCTCGTCCTACTGGTGGGGCTGCATGTACGCCGTCTAGACT [SEQ ID NO: 5] |

TABLE 3-continued

| marker | SNP | Genomic sequence for primer design (5' to 3' direction) |
|---|---|---|
| mME21 377 | [A/ G] | TGTATCAGGAACATAGCCAGCTGCTTTCATCTTCTCTG<u>GCAACGCCTCCA AGAACATGTAGAT</u>TTCCTTG[A/G]CTTGAGGGTGAGATGTATCGCCACCG AGAAACATATGTGCTTTGCCATTTATCTCGATCCAACTGCAACC [SEQ ID NO: 8] |
| mME15 090 | [A/ C] | CATTATGATATCTTTCTCTCAACTCAACCATGAACT<u>CTAAAGCACCATTC CCATCTTTCATCTTT</u>CGGTA[A/C]GCTCGCAAGGCTGTAGAGTAGGATAC GGGAGACAGAGTTAGGCCTTTCTTCGGCATCTCTTCAAGAATGC [SEQ ID NO: 1 and SEQ ID NO: 9] |
| mME36 533 | [G/ T] | CTATAATACTTCAATAAATAACATGCATACATACATA<u>CATGGATAATATA GAGAGAAGACAAGGA</u>TAGCT[G/T]AAGTTTAGTAGTTTTGAAGATGTGAA <u>TCT</u>CGATTTTTATCTACTACACTGTTTGAATGGAATCCTTTTCT [SEQ ID NO: 11] |
| mME13 585 | [C/ T] | CATATTATTCTTAAATAATATAAACCACATAATTATTAAA<u>TTAAATTGAA CTAAAACTACCCTATTTTAA</u>[C/T]GCTTTACAAACTCTTATCTAATGTATGC TTCATTTAATTATTTTTTTGGTTGATACTTTCATTTTATTTT [SEQ ID NO: 12] |

TABLE 4

| marker | SNP | Primer-allele FAM(dye) | Primer-allele VIC(dye) | Probe FAM | Probe VIC | Primer Common |
|---|---|---|---|---|---|---|
| mME12 135 | [A/ G] | GAAGGTGACCAA GTTCATGCT<u>GGTG GCGCTTGTTACGA TCCT</u> | GAAGGTGCGGAGTC AACGGATT<u>GGTGG CGCTTGTTACGATC CC</u> | T | C | AGGAAGCATGT GCTTGAAGGG AGTT |
| mME36 531 | [C/ T] | GAAGGTGACCAA GTTCATGCT<u>CAAA TCCTGTGTTATTG ACTGGTCTC</u> | GAAGGTGCGGAGTC AACGGATT<u>CAAATC CTGTGTTATTGACT GGTCTT</u> | C | T | GGTCCTTCAG CGTAGACCTAA CAAA |
| mME21 377 | [A/ G] | GAAGGTGACCAA GTTCATGCT<u>GGCG ATACATCTCACCC TCAAGT</u> | GAAGGTGCGGAGTC AACGGATT<u>GCGAT ACATCTCACCCTCA AGC</u> | T | C | GCAACGCCTC CAAGAACATGT AGAT |
| mME15 090 | [A/ C] | GAAGGTGACCAA GTTCATGCT<u>ACTC TACAGCCTTGCGA GCT</u> | GAAGGTGCGGAGTC AACGGATT<u>ACTCTA CAGCCTTGCGAGC G</u> | T | C | CTAAAGCACCA TTCCCATCTTT CATCTTT |
| mME36 533 | [G/ T] | GAAGGTGACCAA GTTCATGCT<u>AGAT TCACATCTTCAAA ACTACTAAACTTC</u> | GAAGGTGCGGAGTC AACGGATTG<u>AGATT CACATCTTCAAAAC TACTAAACTTA</u> | C | A | CATGGATAATA TAGAGAGAAGA CAAGGATA |
| mME13 585 | [C/ T] | GAAGGTGACCAA GTTCATGCT<u>GCAT ACATTAGATAAG AGTTTGTAAAGC G</u> | GAAGGTGCGGAGTC AACGGATTA<u>GCAT ACATTAGATAAGA GTTTGTAAAGCA</u> | G | A | TTAAATTGAAC TAAAACTACCC TATTTTAA |

Using the above primers, KASP-assays can be carried out according to standard protocols developed by KBioscience.co.uk (see www.kbioscience.co.uk), in order to detect the presence of either the resistant or susceptible SNP-genotype in homozygous or heterozygous form in plant DNA derived from melon cells or tissues. If the genotype at a given SNP is homozygous, only one fluorescent signal will be detected. If the genotype of the plant at a given SNP is heterozygous, a mixed fluorescent signal will be detected.

For any of the other SNP markers, e.g. mME40332, mME28908, mME9692 and mME50656, similar SNP-genotyping assays can be developed in order to detect the SNP-genotype.

The invention claimed is:

1. A *Cucumis melo* plant, or part thereof, comprising a recombinant chromosome 6, the recombinant chromosome 6 comprising an introgression fragment that confers Melon Yellowing associated Virus (MYaV) resistance onto the *Cucumis melo* plant when present in homozygous or heterozygous form,
wherein said introgression fragment is from a wild plant of the species *Cucumis melo*, a representative sample has been deposited under NCIMB 41966 and wherein said introgression fragment comprises at least two of the following SNP markers:
a) the CC or AC genotype for the SNP marker mME15090 in SEQ ID NO: 1;
b) the GG or AG genotype for the SNP marker mME40332 in SEQ ID NO: 2;
c) the AA or AG genotype for the SNP marker mME12135 in SEQ ID NO: 3;
d) the TT or AT genotype for the SNP marker mME28908 in SEQ ID NO: 4;
e) the TT genotype for the SNP marker mME36531 in SEQ ID NO: 5;
the AA or AT genotype for the SNP marker mME9692 in SEQ ID NO: 6; or
g) the CC or CT genotype for the SNP marker mME50656 in SEQ ID NO: 7; or
wherein said introgression fragment is from a wild plant of the species *Cucumis melo*, a representative sample has been deposited under NCIMB 41969 and wherein said introgression fragment comprises at least two of the following SNP markers:
h) the AA or AG genotype for the SNP marker mME21377 in SEQ ID NO: 8;
i) the CC or AC genotype for the SNP marker mME15090 in SEQ ID NO: 9;
j) the AA or AG genotype for the SNP marker mME12135 in SEQ ID NO: 10;
k) the TT or GT genotype for the SNP marker mME36533 in SEQ ID NO: 11; or
l) the TT or CT genotype for the SNP marker mME13585 in SEQ ID NO: 12.

2. The plant according to claim 1, wherein said plant has an average MYaV disease score of at least 3 on a scale of 1=totally yellow leaves to 9=totally green leaves when grown in an MYaV infested area.

3. The plant according to claim 1, wherein said introgression fragment comprises at least one of the following Single Nucleotide Polymorphism (SNP) markers:

the CC or AC genotype for the SNP marker mME15090 in SEQ ID NO: 1 or in SEQ ID NO: 9; or the AA or AG genotype for the SNP marker mME12135 in SEQ ID NO: 3 or in SEQ ID NO: 10.

4. The plant according to claim 1, wherein said introgression fragment comprises:

the AA or AG genotype for the SNP marker mME21377 in SEQ ID NO: 8.

5. A *Cucumis melo* plant, or part thereof, comprising a recombinant chromosome 6, the recombinant chromosome 6 comprising an introgression fragment that confers Melon Yellowing associated Virus (MYaV) resistance onto the *Cucumis melo* plant when present in homozygous or heterozygous form and wherein said recombinant chromosome 6 is the chromosome 6 present in seeds deposited under accession number NCIMB 42198 or NCIMB 42113.

6. The plant according to claim 1, wherein said introgression fragment comprises at least two of the following SNP markers:

a) the CC or AC genotype for the SNP marker mME15090 in SEQ ID NO: 1;
b) the GG or AG genotype for the SNP marker mME40332 in SEQ ID NO: 2; or
c) the AA or AG genotype for the SNP marker mME12135 in SEQ ID NO: 3.

7. The plant according to claim 1, wherein said introgression fragment comprises at least two of the following SNP markers:

h) the AA or AG genotype for the SNP marker mME21377 in SEQ ID NO: 8;
i) the CC or AC genotype for the SNP marker mME15090 in SEQ ID NO: 9; or
j) the AA or AG genotype for the SNP marker mME12135 in SEQ ID NO: 10.

8. The plant according to claim 1, wherein said plant is an F1 hybrid.

9. The plant according to claim 1, wherein said introgression fragment is equal to or less than 10 Mb in size.

10. Seeds from which a plant according to claim 1 can be grown.

11. A melon fruit harvested from a plant according to claim 1.

12. The plant part of claim 1, wherein the plant part is a plant cell or tissue.

13. A method for producing a *C. melo* plant comprising an introgression fragment on chromosome 6, wherein said introgression fragment comprises an MYaV-resistance allele, comprising:

a) crossing a first melon plant being susceptible to MYaV with a second melon plant being resistant to MYaV, wherein said second melon plant comprises the CC or AC genotype for the SNP marker mME15090 in SEQ ID NO: 1 and the AA or AG genotype for the SNP marker mME12135 in SEQ ID NO: 3;
b) collecting F1 seeds from said cross and backcrossing an F1 plant to the first melon plant to produce a backcross (BC1) population, or selfing said F1 plants one or more times to produce an F2 or F3 population, and
c) optionally selfing the backcross population to produce a BC1S1 population, wherein said F2, F3, BC1 or BC1S1 plant comprises the CC or AC genotype for the SNP marker mME15090 in SEQ ID NO: 1 and the AA or AG genotype for the SNP marker mME12135 in SEQ ID NO: 3.

14. A method for detecting the plant of claim 1, comprising:

a) screening a *Cucumis melo* plant using a molecular marker assay which detects at least one of SNP marker mME15090 in SEQ ID NO: 1 and/or SNP marker mME12135 in SEQ ID NO: 3; and
b) identifying a plant comprising at least the CC or AC genotype for the SNP marker mME15090 in SEQ ID NO: 1 and/or the AA or AG genotype for the SNP marker mME12135 in SEQ ID NO: 3.

15. A method of producing *C. melo* F1 hybrid plants comprising a MYaV resistance phenotype comprising:

a) crossing a first inbred melon plant comprising at least one recombinant chromosome 6, the recombinant chromosome 6 comprising an introgression fragment that confers Melon Yellowing associated Virus (MYaV) resistance onto the first inbred melon plant when present in homozygous or heterozygous form and wherein said recombinant chromosome 6 is the chromosome 6 present in seeds deposited under accession number NCIMB 42198 or NCIMB 42113, with a second inbred melon plant with or without said at least one recombinant chromosome 6 and
b) collecting F1 hybrid seeds from said cross.

16. A method for producing a melon plant comprising MYaV resistance on chromosome 6, said method comprising:

a) screening a wild melon accession or several wild melon accessions using a molecular marker assay which detects at least one of SNP marker mME15090 in SEQ ID NO: 1 and/or SNP marker mME12135 in SEQ ID NO: 3; and
b) identifying and/or selecting a wild melon plant comprising at least the CC or AC genotype for the SNP marker mME15090 in SEQ ID NO: 1 and/or the AA or AG genotype for the SNP marker mME12135 in SEQ ID NO: 3; and
c) optionally confirming MYaV resistance in an MYaV resistance assay; and
d) introgressing said MYaV resistance from said wild accession into a melon plant.

17. The plant or plant part of claim 1, wherein the plant is a variety, breeding line, or cultivar of *Cucumis melo*.

18. A part of a seed according to claim 10, wherein said part is a cell or tissue.

19. The plant according to claim 1, wherein the plant is a vegetatively propagated plant.

20. An F1 melon plant produced by crossing the plant of claim 1 with another melon plant.

21. A *Cucumis melo* plant, or part thereof, comprising a recombinant chromosome 6, the recombinant chromosome 6 comprising an introgression fragment that confers Melon Yellowing associated Virus (MYaV) resistance onto the *Cucumis melo* plant when present in homozygous or heterozygous form and wherein said introgression fragment comprises the following two Single Nucleotide Polymorphism (SNP) markers:

a) the CC or AC genotype for the SNP marker mME15090 in SEQ ID NO: 1; and
b) the AA or AG genotype for the SNP marker mME12135 in SEQ ID NO: 3, and wherein said introgression fragment is from a wild plant of the species *Cucumis melo*.

22. The plant according to claim 1, wherein said introgression fragment is equal to or less than 8 Mb in size.

23. The plant according to claim 1, wherein said introgression fragment comprises the following SNP markers:

a) the CC or AC genotype for the SNP marker mME15090 in SEQ ID NO: 1;

b) the GG or AG genotype for the SNP marker mME40332 in SEQ ID NO: 2; and c) the AA or AG genotype for the SNP marker mME12135 in SEQ ID NO: 3.

24. The plant according to claim 1, wherein said introgression fragment comprises the following SNP markers:
h) the AA or AG genotype for the SNP marker mME21377 in SEQ ID NO: 8;

i) the CC or AC genotype for the SNP marker mME15090 in SEQ ID NO: 9; and j) the AA or AG genotype for the SNP marker mME12135 in SEQ ID NO: 10.

25. A method of producing *C. melo* F1 hybrid plants comprising a MYaV resistance phenotype comprising:

i) crossing a first inbred melon plant comprising a recombinant chromosome 6 in homozygous form, the recombinant chromosome 6 comprising an introgression fragment that confers Melon Yellowing associated Virus (MYaV) resistance onto the *Cucumis melo* plant, wherein said introgression fragment is from a wild plant of the species *Cucumis melo*, a representative sample has been deposited under NCIMB 41966 and wherein said introgression fragment comprises at least two of the following SNP markers:

a) the CC genotype for the SNP marker mME15090 in SEQ ID NO: 1;

b) the GG genotype for the SNP marker mME40332 in SEQ ID NO: 2;

c) the AA genotype for the SNP marker mME12135 in SEQ ID NO: 3;

d) the TT genotype for the SNP marker mME28908 in SEQ ID NO: 4;

e) the TT genotype for the SNP marker mME36531 in SEQ ID NO: 5;

f) the AA genotype for the SNP marker mME9692 in SEQ ID NO: 6; or g) the CC genotype for the SNP marker mME50656 in SEQ ID NO: 7; or wherein said introgression fragment is from a wild plant of the species *Cucumis melo*, a representative sample has been deposited under NCIMB 41969 and wherein said introgression fragment comprises at least two of the following SNP markers:

h) the AA genotype for the SNP marker mME21377 in SEQ ID NO: 8;

i) the CC genotype for the SNP marker mME15090 in SEQ ID NO: 9;

j) the AA genotype for the SNP marker mME12135 in SEQ ID NO: 10;

k) the TT genotype for the SNP marker mME36533 in SEQ ID NO: 11; or l) the TT genotype for the SNP marker mME13585 in SEQ ID NO: 12 with a second inbred melon plant with or without said introgression fragment and ii) collecting F1 hybrid seeds from said cross.

* * * * *

SEQUENCE LISTING

```
<160> NUMBER OF SEQ ID NOS: 30

<210> SEQ ID NO 1
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME15090

<400> SEQUENCE: 1
cattatgata tctttctctc aactcaacca tgaactctaa agcaccattc ccatctttca      60
tctttcggta cgctcgcaag gctgtagagt aggatacggg agacagagtt aggcctttct    120
tcggcatctc ttcaagaatg c                                               141

<210> SEQ ID NO 2
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME40332

<400> SEQUENCE: 2
ttgctgcaaa gccaccaact ccaggaattg ttagcagagg aattgctttg gagggtttct      60
gtagtatctt ggctggactc tggggtacag gtgccggatc aactacttta acggaaaatg    120
tacatactat tcatgtaaca a                                               141

<210> SEQ ID NO 3
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: mME12135

<400> SEQUENCE: 3
tgccagccgc acgtttcatc ttttggtaat aactattaaa agcataggaa gcatgtgctt      60
gaagggagtt aggatcgtaa caagcgccac cctgttgaat ggaacggcaa tcagcctgtc    120
cttcaccaca agcatagtcc a                                               141

<210> SEQ ID NO 4
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME28908

<400> SEQUENCE: 4
tccaatgtca tattttgatc cgcagcattt gccttcatct ggttgagttt agaataacaa      60
```
acgtcagtat taaattacaa caaaccagck atattaccaa aaagaaaaca atcaatcaga    120
taaggaaaac ctgaktggat t                                              141

<210> SEQ ID NO 5
<211> LENGTH: 139
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME36531

<400> SEQUENCE: 5
ctgttgaaat atattatgcc gttattttct tggaatattt gctgtcaaat cctgtgttat    60
tgactggtct tttttgttag gtctacgctg aaggaccagc tcgtcctact ggtggggctg    120
catgtacgcc gtctagact                                                 139

<210> SEQ ID NO 6
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME9692

<400> SEQUENCE: 6
aagcacccct gtcattattt tgcataatct cacaaagtcc cccatcaaca gaaccttctt    60
caacattgtc atcctcgcct atatcatcat ctraaccaga cacttccttc tccaactgag    120
gattgtaygt ccattccaat c                                              141

<210> SEQ ID NO 7
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME50656

<400> SEQUENCE: 7
aaaaggggaa gcaaaaagtt tcgaaggaat cgcatgtttc tgaagctctt gataagctca    60
gagagcagac cagagaggcg gttaaggggc ttgaatcagt gtcaggtcct aaacctggtg    120
ttgatgaatt tggtaaagat g                                              141

<210> SEQ ID NO 8
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME21377

<400> SEQUENCE: 8
tgtatcagga acatagccag ctgctttcat cttctctggc aacgcctcca agaacatgta    60
gatttccttg acttgagggt gagatgtatc gccaccgaga aacatatgtg ctttgccatt    120
tatctcgatc caactgcaac c                                              141

<210> SEQ ID NO 9
<211> LENGTH: 141

```
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME15090

<400> SEQUENCE: 9
cattatgata tctttctctc aactcaacca tgaactctaa agcaccattc ccatctttca      60
tctttcggta cgctcgcaag gctgtagagt aggatacggg agacagagtt aggccttct     120 tcggcatctc ttcaagaatg c                                              141

<210> SEQ ID NO 10
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME12135

<400> SEQUENCE: 10
tgccagccgc acgtttcatc ttttggtaat aactattaaa agcataggaa gcatgtgctt      60
gaagggagtt aggatcgtaa caagcgccac cctgttgaat ggaacggcaa tcagcctgtc     120
cttcaccaca agcatagtcc a                                              141

<210> SEQ ID NO 11
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME36533

<400> SEQUENCE: 11
ctataatact tcaataaata acatgcatac atacatacat ggataatata gagagaagac      60
aaggatagct taagtttagt agttttgaag atgtgaatct cgattttat ctactacact     120 gtttgaatgg aatccttttc t                                              141

<210> SEQ ID NO 12
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME13585

<400> SEQUENCE: 12
catattattc ttaaataata taaaccacat aattattaaa ttaaattgaa ctaaaactac      60
cctattttaa tgcttacaa actcttatct aatgtatgct tcatttaatt attttttgg     120 ttgatacttt cattttattt t                                              141

<210> SEQ ID NO 13
<211> LENGTH: 42
<212> TYPE: DNA
<213> ORGANISM: Artificial Sequence
<220> FEATURE:
<223> OTHER INFORMATION: mME12135 primer - allele FAM(dye)

<400> SEQUENCE: 13
```

```
gaaggtgacc aagttcatgc tggtggcgct tgttacgatc ct                42

<210> SEQ ID NO 14
<211> LENGTH: 42
<212> TYPE: DNA
<213> ORGANISM: Artificial Sequence
<220> FEATURE:
<223> OTHER INFORMATION: mME12135 pprimer -allele VIC(dye)

<400> SEQUENCE: 14
gaaggtcgga gtcaacggat tggtggcgct tgttacgatc cc                42

<210> SEQ ID NO 15
<211> LENGTH: 25
<212> TYPE: DNA
<213> ORGANISM: Artificial Sequence
<220> FEATURE:
<223> OTHER INFORMATION: mME12135 Primer Common

<400> SEQUENCE: 15
aggaagcatg tgcttgaagg gagtt                                   25

<210> SEQ ID NO 16
<211> LENGTH: 47
<212> TYPE: DNA
<213> ORGANISM: artificial sequence
<220> FEATURE:
<223> OTHER INFORMATION: mME36531

<400> SEQUENCE: 16
gaaggtgacc aagttcatgc tcaaatcctg tgttattgac tggtctc           47

<210> SEQ ID NO 17
<211> LENGTH: 47
<212> TYPE: DNA
<213> ORGANISM: Artificial Sequence
<220> FEATURE:
<223> OTHER INFORMATION: mME36531 Primer allele VIC(dye)

<400> SEQUENCE: 17
gaaggtcgga gtcaacggat tcaaatcctg tgttattgac tggtctt           47

<210> SEQ ID NO 18
<211> LENGTH: 25
<212> TYPE: DNA
<213> ORGANISM: Artificial Sequence
<220> FEATURE:
<223> OTHER INFORMATION: mME36531 Primer Common

<400> SEQUENCE: 18
ggtccttcag cgtagaccta acaaa                                   25

<210> SEQ ID NO 19
<211> LENGTH: 44
<212> TYPE: DNA
<213> ORGANISM: Artificial Sequence
<220> FEATURE:
<223> OTHER INFORMATION: mME21377 Primer allele FAM(dye)

<400> SEQUENCE: 19
gaaggtgacc aagttcatgc tggcgataca tctcaccctc aagt              44

<210> SEQ ID NO 20
<211> LENGTH: 43
<212> TYPE: DNA
<213> ORGANISM: Artificial Sequence
```

```
<220> FEATURE:
<223> OTHER INFORMATION: mME21377 Primer allele VIC(dye)

<400> SEQUENCE: 20
gaaggtcgga gtcaacggat tgcgatacat ctcaccctca agc                 43

<210> SEQ ID NO 21
<211> LENGTH: 25
<212> TYPE: DNA
<213> ORGANISM: Artificial Sequence
<220> FEATURE:
<223> OTHER INFORMATION: mME21377 Primer Common

<400> SEQUENCE: 21
gcaacgcctc caagaacatg tagat                                     25

<210> SEQ ID NO 22
<211> LENGTH: 41
<212> TYPE: DNA
<213> ORGANISM: Artificial Sequence
<220> FEATURE:
<223> OTHER INFORMATION: mME15090 Primer allele FAM(dye)

<400> SEQUENCE: 22
gaaggtgacc aagttcatgc tactctacag ccttgcgagc t                   41

<210> SEQ ID NO 23
<211> LENGTH: 41
<212> TYPE: DNA
<213> ORGANISM: Artificial Sequence
<220> FEATURE:
<223> OTHER INFORMATION: mME15090 Primer allele VIC(dye)

<400> SEQUENCE: 23
gaaggtcgga gtcaacggat tactctacag ccttgcgagc g                   41

<210> SEQ ID NO 24
<211> LENGTH: 29
<212> TYPE: DNA
<213> ORGANISM: Artificial Sequence
<220> FEATURE:
<223> OTHER INFORMATION: mME15090 Primer Common

<400> SEQUENCE: 24
ctaaagcacc attcccatct ttcatctttt                                29

<210> SEQ ID NO 25
<211> LENGTH: 51
<212> TYPE: DNA
<213> ORGANISM: Artificial Sequence
<220> FEATURE:
<223> OTHER INFORMATION: mME36533 Primer alllel FAM(dye)

<400> SEQUENCE: 25
gaaggtgacc aagttcatgc tagattcaca tcttcaaaac tactaaactt c        51

<210> SEQ ID NO 26
<211> LENGTH: 52
<212> TYPE: DNA
<213> ORGANISM: Artificial Sequence
<220> FEATURE:
<223> OTHER INFORMATION: mME36533 Primer allele VIC(dye)

<400> SEQUENCE: 26
gaaggtcgga gtcaacggat tgagattcac atcttcaaaa ctactaaact ta       52
```

```
<210> SEQ ID NO 27
<211> LENGTH: 30
<212> TYPE: DNA
<213> ORGANISM: Artificial Sequence
<220> FEATURE:
<223> OTHER INFORMATION: mME36533 Primer Common

<400> SEQUENCE: 27
catggataat atagagagaa gacaaggata                                        30

<210> SEQ ID NO 28
<211> LENGTH: 50
<212> TYPE: DNA
<213> ORGANISM: Artificial Sequence
<220> FEATURE:
<223> OTHER INFORMATION: mME13585 Primer allele FAM(dye)

<400> SEQUENCE: 28
gaaggtgacc aagttcatgc tgcatacatt agataagagt ttgtaaagcg                  50

<210> SEQ ID NO 29
<211> LENGTH: 51
<212> TYPE: DNA
<213> ORGANISM: Artificial Sequence
<220> FEATURE:
<223> OTHER INFORMATION: mME13585 Primer allele VIC(dye)

<400> SEQUENCE: 29
gaaggtcgga gtcaacggat tagcatacat tagataagag tttgtaaagc a                51

<210> SEQ ID NO 30
<211> LENGTH: 30
<212> TYPE: DNA
<213> ORGANISM: Artificial Sequence
<220> FEATURE:
<223> OTHER INFORMATION: mME13585 Primer Common

<400> SEQUENCE: 30
ttaaattgaa ctaaaactac cctattttaa                                        30
```